United States Patent [19]

Vahlne et al.

[11] Patent Number: 5,346,989
[45] Date of Patent: Sep. 13, 1994

[54] PEPTIDES FOR USE IN INDUCTION OF T CELL ACTIVATION AGAINST HIV-1

[75] Inventors: Anders Vahlne, Hovas; Bo Svennerholm, Gothenburg; Lars Rymo, Hovas; Stig Jeansson, Gothenburg; Peter Horal, Gothenburg; Cecil Czerkinsky, Gothenburg; Jan Holmgren, Vastra Frolunda, all of Sweden

[73] Assignee: Syntello Vaccine Development KB, Gothenburg, Sweden

[21] Appl. No.: 121,032

[22] Filed: Sep. 13, 1993

Related U.S. Application Data

[63] Continuation of Ser. No. 709,709, Jun. 3, 1991, Pat. No. 5,272,251, which is a continuation-in-part of Ser. No. 571,080, Aug. 22, 1990, abandoned.

[51] Int. Cl.$^5$ .................... A61K 37/02; A61K 39/12; A61K 37/00; C07K 5/00
[52] U.S. Cl. .................................. 530/324; 530/325; 424/188.1; 424/208.1
[58] Field of Search .................. 530/324, 325; 424/89; 514/14

[56] References Cited

U.S. PATENT DOCUMENTS

4,943,628  7/1990  Rosen et al. .................... 530/326

FOREIGN PATENT DOCUMENTS

| | | | |
|---|---|---|---|
| 273716 | 12/1987 | European Pat. Off. | C07K 7/08 |
| 0265785 | 5/1988 | European Pat. Off. | C12N 15/00 |
| 330359 | 2/1989 | European Pat. Off. | C07K 7/08 |
| 339504 | 4/1989 | European Pat. Off. | C07K 7/00 |
| 459779 | 5/1991 | European Pat. Off. | C12P 21/08 |
| 86/02383 | 4/1986 | PCT Int'l Appl. | C12P 21/00 |
| 87/07616 | 12/1987 | PCT Int'l Appl. | C07K 7/08 |
| 88/10267 | 12/1988 | PCT Int'l Appl. | C07K 7/04 |
| 89/05820 | 6/1989 | PCT Int'l Appl. | C07K 7/08 |
| 89/10416 | 11/1989 | PCT Int'l Appl. | C12A 1/70 |
| 91/04045 | 4/1991 | PCT Int'l Appl. | A61K 37/02 |
| WO9204462 | 3/1992 | PCT Int'l Appl. | C12P 21/02 |
| 92/05800 | 4/1992 | PCT Int'l Appl. | A01K 39/21 |
| 8800471 | 1/1988 | World Int. Prop. O. | A61K 39/12 |

OTHER PUBLICATIONS

Alizon, et al., 1986 "Gemehc variability of the AIDS virus: . . ." Cell vol. 46: 63–74.

Ho, et al., 1988, "Second conserved domain of gp120 is important . . ." Science 239: 1021–1023.

Manca, F., "The Naive Repertoire of Human T Helper Cells Specific for gp230, the Envelope Glycoprotein of HIV", *J. Immunol*, Mar. 15, 1991, pp. 1964–1971 (Abstract only).

M. Clerici, "Immunization with subunit human immunodeficiency virus vaccine generates stronger T helper cell immunity than natural infection", *Eur J. Immunol*, pp. 1345–1349, Jun. 1991.

McDougal, J. S. et al., "HIV Binding to the CD4 Molecule: Conformation Dependence and Binding Inhibition Studies", *Human Retroviruses, Cancer, and AIDS*, Symposium hel at Keystone, CO, Apr. 1987.

Kenealy, W. et al., "Antibodies from Human Immunodeficiency Virus–Infected Individuals Bind to a Short Amino Acid Sequence that Elicits Neutralizing Antibodies in Animals", *Aids Research and Human Retroviruses*, vol. 5, No. 2 1989.

Wahren, B., "HIV-1 Peptides Induce a Proliferative Response in Lymphocytes from Infected Persons", *Journal of Acquired Immune Deficiency Syndromes*, vol. 2, No. 5, pp. 448–456, 1989.

Modrow, S. et al., "Use of Synthetic Oligopeptides in Indentification and Characterization of Immunological Functions in the Amino Acid Sequence of the Envelope Protein of HIV-1", *Journal of Acquired Immune Deficiency Syndromes*, vol. 2, No. 1, 1989.

Krychnak, V. et al., "Color-Monitored Solid-Phase (List continued on next page.)

*Primary Examiner*—Christine M. Nucker
*Assistant Examiner*—Lynette R. F. Smith
*Attorney, Agent, or Firm*—Knobbe, Martens, Olson & Bear

[57] ABSTRACT

Peptides corresponding to regions of the human immunodeficiency virus protein gp-120 are provided for eliciting T-cell activation.

11 Claims, 2 Drawing Sheets

OTHER PUBLICATIONS

Multiple Peptide Synthesis Under Low-Pressure Continuous-Flow Conditions", *Peptide Research*, vol. 3 No. 4, 1990.

Neurath, A. et al., "B cell epitope mapping of human immunodeficiency virus envelope glycoproteins with long (19- to 36-reside) synthetic peptides", *Journal of General Virology*, pp. 85–95, 1990.

Dadaglio, G. et al., "Epitope Recognition of Conserved HIV Envelope Sequences by Human Cytotoxic T Lymphocytes", *Journal of Immunology* vol. 147, 2302–2309, No. 7, Oct. 1, 1991.

Neurath, A. et al., "Peptides Mimicking Selected Disulfide Loops in HIV-1 gp120, Other Than V3, Do Not Elicit Virus-Neutralizing Antibodies", *Aids Research and Human Retroviruses*, vol. 7, No. 8, 1991.

Vahlne, A. et al., "Immunizations of Monkeys with Synthetic Peptides Disclose Conserved Areas on gp120 of Human Immunodeficiency Virus Type 1 Associated with Cross-Neutralizing Antibodies and T-cell Recognition", *Proc. Natl. Acad. Sci, USA*, vol. 88, pp. 10744–10748, Dec. 1991.

Barre-Sinoussi et al., "Isolation of a T-Lymphotropic Retrovirus from a Patient at Risk for Acquired Immune Deficiency Syndrome (AIDS)", Science, 220:868 (1983).

Gallo et al., "Frequent Detection and Isolation of Cytopathic Retroviruses (HTLV-III) from Patients with AIDS and at Risk for AIDS", Science, 224:500 (1984).

Allan et al., "Major Glycoprotein Antigens That Induce Antibodies in AIDS Patients Are Encoded by HTLV-III", Science, 228:1091–1094 (1985).

Barin et al., "Virus Envelope Protein of HTLV-III Represents Major Target Antigen for Antibodies in AIDS Patients", Science, 228:1094–1096 (1985).

Cabradilla et al., "Serodiagnosis of Antibodies to the Human AIDS Retrovirus With a Bacterially Synthesized env Polypeptide", Biotechnology, 4:128–133 (1986).

Chang et al., "Detection of Antibodies to Human T-Cell Lymphotropic Virus-III (HTLV-III) With An Immunoassay Employing a Recombinant Escherichia Coli-Derived Viral Antigenic Peptide", Biotechnology, 3:905–909 (1985).

Kennedy et al., "Antiserum to a Synthetic Peptide Recognizes the HTLV-III Envelope Glycoprotein", Science, 231:1556–1559 (1986).

Ranki et al., "Neutralizing antibodies in HIV (HTLV-III) Infection: Correlation With Clinical Outcome and Antibody Response Against Different Viral Proteins", Clin. Exp. Immunol., 69:231 (1987).

Marx, "New Hope on the AIDS Vaccine Front", Science, 224:1254 (1989).

Reinherz et al., "The Characterization and Function of Human Immunoregulatory T Lymphocyte Subsets", Immunol. Today, 2:69 (1981).

Burns et al., "Thymus Dependence of Viral Antigens", Nature, 256:654 (1975).

Askonas et al., "Cytotoxic T-Memory Cells in Virus Infection and the Specificity of Helper T Cells", Immunology, 45:79 (1982).

Berkower et al., "A Possible Immunodominant Epitope Recognized By Murine T Lymphocytes Immune to Different Myoglobins", Proc. Natl. Acad. Sci. U.S.A., 79:4723–4727 (1982).

DeLisi et al., "T-Cell Antigenic Sites Tend to be Amphipathic Structures", Proc. Natl. Acad. Sci. U.S.A., 82:7048–7052 (1985).

Margalit et al., "Prediction of Immunodominant Helper T Cell Antigenic Sites From The Primary Sequence", J. Immunol., 138:2213–2229 (1987).

Milich et al., "Nonoverlapping T and B Cell Determinants on an Hepatitis B Surface Antigen Pre-S(2) Region Synthetic Peptide", J. Exp. Med., 164:532–547 (1986).

Krzych et al., "Induction of Helper and Suppressor T Cells by Nonoverlapping Determinants on the Large Protein Antigen, $\beta$-Galactosidase", FASEB. J., 2:141–145 (1988).

Terpstra et al., "Longitudinal Study of Leukocyte Functions In Homosexual Men Seroconverted for HIV:Rapid and Persistent Loss of B Cell Function After HIV Infection", Eur. J. Immunol., 19:667–673 (1989).

Fahey et al., "Quantitative Changes in T Helper Or T Suppressor/Cytotoxic Lymphocyte Subsets That Distinguish Acquired Immune Deficiency Syndrome from Other Immune Subset Disorders", JAMA, 76:95–100 (1984).

Shearer et al., "Functional T Lymphocyte Immune Deficiency Syndrome in a Population of Homosexual Men Who do Not Exhibit Symptoms of Acquired Immune Deficiency Syndrome", J. Clin. Invest., 74:496–506 (1984).

Giorgi et al., "Early Effects of HIV on CD4 Lympho- (List continued on next page.)

OTHER PUBLICATIONS cytes In Vivo", J. Immunol., 138:3725–3730 (1987).

van Noesel et al., "Functional and Phenotypic Evidence for a Selective Loss of Memory T Cells in Asymptomatic Human Immuno-deficiency Virus—infected Men", J. Clin. Invest., 86:293–299.

Milich et al., "A Single 10-Residue Pre-S(1) Peptide Can Prime T Cell Help For Antibody Production To Multiple Epitopes Within The Pre-S(1), Pre-S(2) And S Regions of HBsAg¹", J. Immunol., 138:4457 (1987).

Kennedy et al., "Antiserum to a Synthetic Peptide Recognizes the HTLV-III Envelope Glycoprotein", Science, 231:1556–1559 (1986).

Bolognesi, "HIV Antibodies and Vaccine Design", AIDS, 3:S111–S118 (1989).

Javaherian et al., "Broadly Neutralizing Antibodies Elicited by the Hypervariable Neutralizing Determinant of HIV-1", Science, 250:1590–1593 (1990).

Rusche et al., "Antibodies that Inhibit Fusion of Human Immunodeficiency Virus-Infected Cells Bind a 24-Amino Acid Sequence of the Viral Envelope, gp120", Proc. Natl. Acad. Sci. USA, 85:3198–3202 (1988).

Lerner et al., in, The Biology of Immunological Disease: A Hospital Practice Book, (Dixon and Fisher, eds.) pp. 331–338 (1983).

Lerner, "Antibodies of Predetermined Specificity in Biology and Medicine", Adv. Immunol., 36:1–44 (1984).

Van Regenmortel, "Synthetic Peptides As Viral Vaccines", Ann. Inst. Pasteur Virol., 137E:497–528 (1986).

Erickson and Merrifield in The Proteins, 3rd Edit., vol. 2, Academic Press, New York, Chapter 3 (1976).

Cianciolo et al., "Macrophage Accumulation in Mice is Inhibited by Low Molecular Weight Products From Murine Leukemia Viruses", J. Immunol., 124:2900–2905 (1980).

Cianciolo et al., "Inhibition of Lymphocyte Proliferation by a Synthetic Peptide Homologous to Retroviral Envelope Proteins", Nature, 230:453–455 (1985).

Steward et al., "Synthetic Peptides: A Next Generation of Vaccines?", Immunol. Today, 8:51–58 (1987).

Berman et al., "Protection of Chimpanzees From Infection by HIV-1 After Vaccination with Recombinant Glycoprotein gp120 but not gp160", Nature, 345:622–625 (1990).

Ho et al., "Second Conserved Domain of gp120 Is Important for HIV Infectivity and Antibody Neutralization", Science, 239:1021–1023 (1988).

Muesing et al., "Nucleic Acid Structure and Expression of the Human AIDS/Lymphadenopathy Retrovirus", Nature, 313:450–458 (1985).

Mierke et al., "Morphiceptin Analogs Containing 2-Aminocyclopentane Carboxylic Acid as a Peptidomimetic for Proline", Int. J. Peptide Protein Res., 35:35–45 (1990).

Portoghese et al., "Design of Peptidomimetic S Opioid Receptor Antagonists Using the Message-Address Concept", J. Med. Chem., 33:1714–1720 (1990).

Goodman et al., "Peptidomimetics: Synthesis, Spectroscopy, and Computer Simulations", Biopolars, 26:S25–S32 (1987).

Barany and Merrifield, The Peptides: Analysis, Synthesis, Biology, vol. 1, Gross and Meinenhofer, eds., Academic Press, New York, Chap. 1 (1980).

Sanchez et al., "Recombinant System For Overexpression of Cholera Toxin B Subunit in Vibrio Cholerae as a Basis for Vaccine Development", Proc. Natl. Acad. Sci USA, 86:481–485 (1989).

Takahashi et al., "Induction of CD8+ Cytotoxic T Cells by Immunization With Purified HIV-1 Envelope Protein in ISCOMs", Nature, 344:873–875 (1990).

Bergot et al., "Utility of Trifluoromethane Sulfonic Acid as a Cleavage Reagent in Solid Phase Peptide Synthesis", Applied Biosystems User Bulletin, Peptide Synthesizer, Issue No. 16, Sep. 2, 1986.

Kaplan and Clark, "An Improved Rosetting Assay For Detection Of Human T Lymphocytes", J. Immunol. Met. 6:131–135 (1974).

Gillis et al., "T Cell Growth Factor: Parameters of Production and a Quantitative Microassay For Activity", J. Immunol., 120:2027–2032 (1978).

Jeansson et al., "Elimination of Mycoplasmas from Cell Cultures Utilizing Hyperimmune Sera", Ex. Cell Res., 161:181–188 (1985).

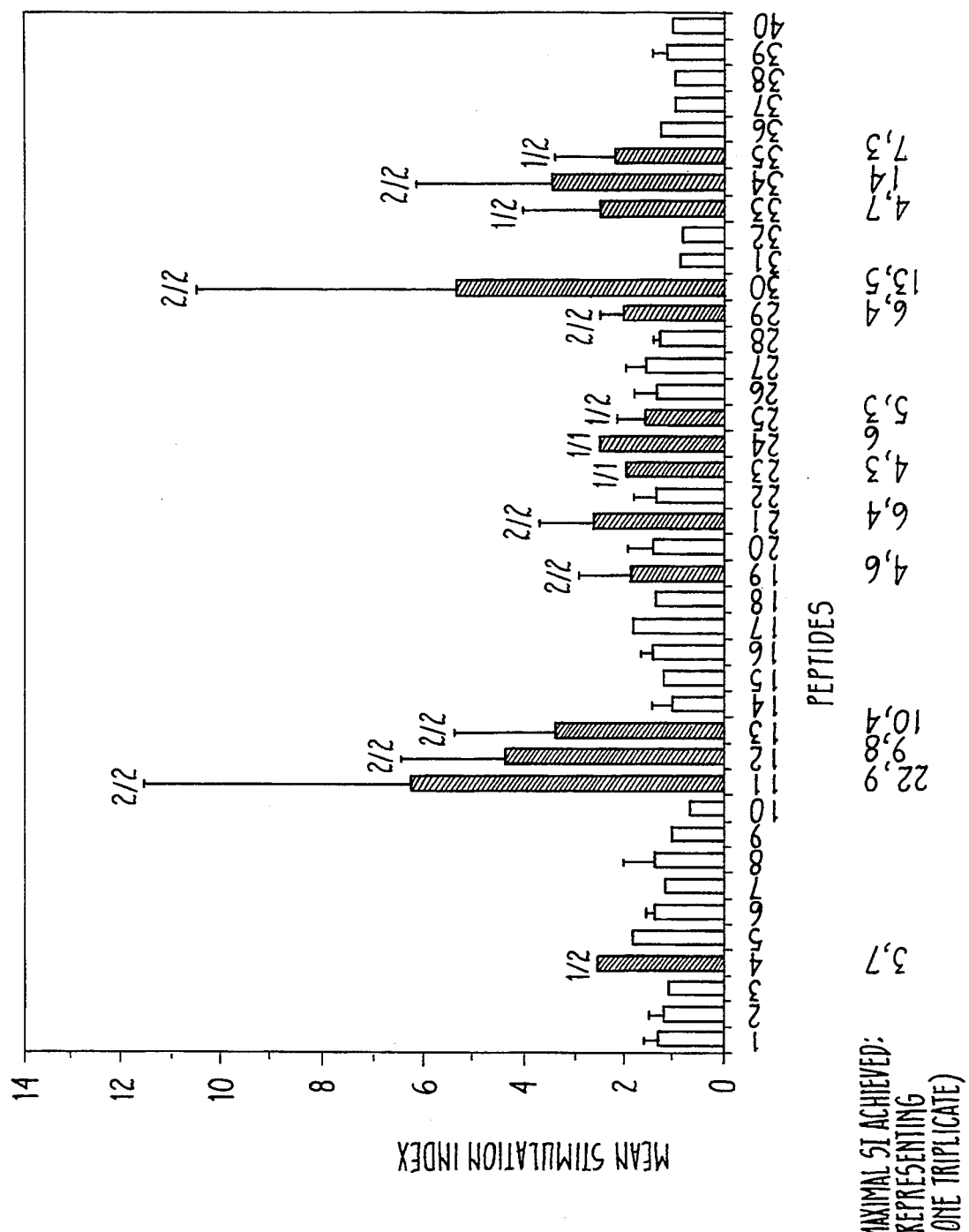

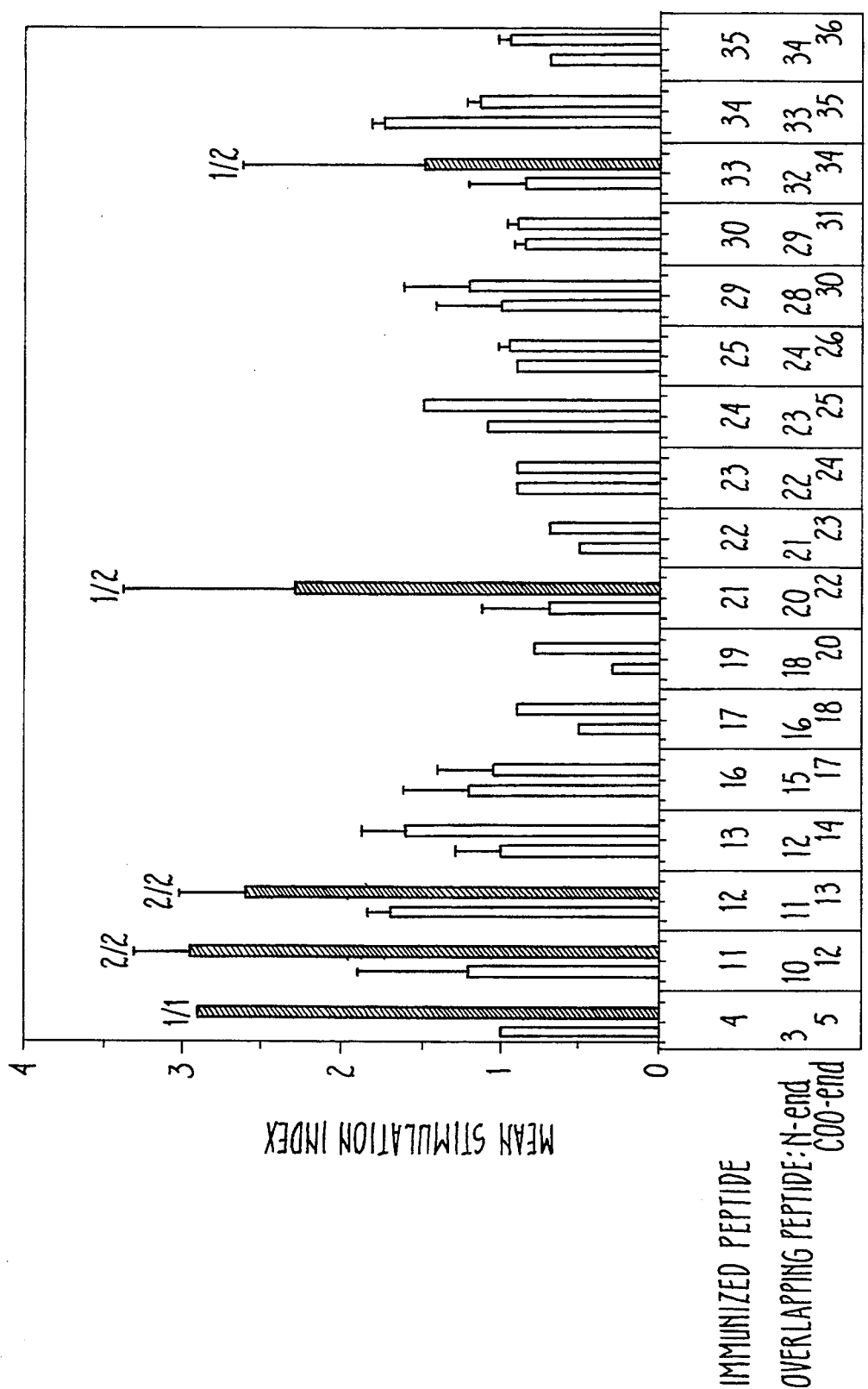

PEPTIDES FOR USE IN INDUCTION OF T CELL ACTIVATION AGAINST HIV-1

This application is a continuation of patent application Ser. No. 07/709,709, filed Jun. 3, 1991, which is a continuation-in-part of U.S. patent application Ser. No. 07/571,080, filed Aug. 22, 1990, now abandoned.

BACKGROUND OF THE INVENTION

AIDS and AIDS-related disorders (ARC) are caused by a retrovirus, the human immunodeficiency virus (HIV). Barré-Sinoussi et al., "Isolation of a T-Lymphotropic Retrovirus from a Patient at Risk for Acquired Immune Deficiency Syndrome (AIDS), Science, 220:868 (1983); and Gallo et al., "Frequent Detection and Isolation of Cytopathic Retroviruses (HTLV-III) From Patients with AIDS and at Risk for AIDS", Science, 224:500 (1984).

Like most viruses, HIV often elicits the production of neutralizing antibodies. Unlike many other viruses and other infectious agents for which infection leads to protective immunity, however, HIV specific antibodies are insufficient to halt the progression of the disease. Therefore, in the case of HIV, a vaccine that elicits the immunity of natural infection could prove to be ineffective. In fact, vaccines prepared from the HIV protein gp160 appear to provide little immunity to HIV infection although they elicit neutralizing antibodies. The failure to produce an effective anti-HIV vaccine has led to the prediction that an effective vaccine will not be available until the end of the 1990's.

The HIV genome has been well characterized. Its approximately 10Kb encodes sequences that contain regulatory segments for HIV replication as well as the gag, pol and env genes coding for the core proteins, the reverse transcriptase-protease-endonuclease, and the internal and external envelope glycoproteins respectively.

The HIV env gene encodes the intracellular glycoprotein, gp160, which is normally processed by proteolytic cleavage to form gp120, the external viral glycoprotein, and gp41, the viral transmembrane glycoprotein. The gp120 protein remains associated with HIV virions by virtue of noncovalent interactions with gp41. These noncovalent interactions are weak, consequently most of the gp120 is released from cells and virions in a soluble form.

Previous studies have shown that the proteins encoded by the gag and especially the env regions of the HIV-1 genome are immunogenic since antibodies to the products of the gag and env genes are found in the sera of HIV infected, AIDS and ARC patients.

It has previously been shown that some antibodies obtained from sera of AIDS and ARC patients, as well as asymptomatic individuals infected with the virus are specific to gp120 and gp160. Occasionally these antibodies are neutralizing. The envelope glycoproteins are the HIV-1 antigen most consistently recognized by antibodies in AIDS and ARC patient sera. Allan et al., "Major Glycoprotein Antigens that Induce Antibodies in AIDS Patients are Encoded by HTLV-III", Science, 228:1091-1094 (1985); and Barin et al., "Virus Envelope Protein of HTLV-III Represents Major Target Antigen for Antibodies in AIDS Patients", Science, 228:1094-1096 (1985). In addition, antibodies in patient sera also recognize epitopes of the viral core proteins encoded by the gag gene.

Immunologically important HIV-1 antigens for use in diagnosis and as potential vaccine compositions have been prepared by cloning portions of the HIV-1 genome in various expression systems such as bacteria, yeast or vaccinia. Cabradilla et al., "Serodiagnosis of Antibodies to the Human AIDS Retrovirus With a Bacterially Synthesized env Polypeptide", Biotechnology, 4:128-133 (1986); and Chang et al., "Detection of Antibodies to Human T-Cell Lymphotropic Virus-III (HTLV-III) With an Immunoassay Employing a Recombinant *Escherichia coli* - Derived Viral Antigenic Peptide", Biotechnology, 3:905-909 (1985). HIV-1 antigens produced by recombinant DNA methods, however, must still be exhaustively purified to avoid adverse reactions upon vaccination and false positive reactions in ELISA assays due to any antibody reactivity to antigens of the expression system which may contaminate the HIV-1 antigen preparation. Also, denaturation of HIV-1 antigens during purification may destroy important antigen activity. Preparation of proteins from intact viruses can also result in contamination by the virus.

Several publications have presented data showing immunologic reactivity of selected synthetic peptides corresponding to portions of the antigenic proteins of HIV-1. In one study, a peptide having the amino acid sequence Tyr-Asp-Arg-Pro-Glu-Gly-Ile-Glu-Glu-Glu-Gly-Gly-Glu-Arg-Asp-Arg -Asp-Arg-Ser-Gly-Cys which corresponds to amino acid residues 735-752 of HIV-1 was synthesized. Kennedy et al., "Antiserum to a Synthetic Peptide Recognizes the HTLV-III Envelope Glycoprotein", Science, 231:1556-1559 (1986). This peptide, derived from a portion of gp41, was used to immunize rabbits in an attempt to elicit a neutralizing antibody response to HIV-1. Furthermore, several sera from AIDS patients known to contain anti-gp41 antibodies were weakly reactive with this peptide, thus indicating that this peptide contains at least one epitope recognized, to some extent, by antibodies to native gp160/gp41. However, this peptide has not been shown to elicit neutralizing antibodies in mammals other than rabbits nor has it been suggested for use as a human vaccine.

Longitudinal studies conducted on cohorts of HIV-infected individuals have indicated that a stable clinical condition is associated with presence of high titers of neutralizing antibodies against the envelope glycoprotein gp120 of HIV and especially against a specific segment of eight amino acids. Ranki et al., "Neutralizing Antibodies in HIV (HTLV-III) Infection: Correlation with Clinical Outcome and Antibody Response Against Different Viral Proteins", Clin. Exp. Immunol., 69:231 (1987); and Marx (1989).

Achieving protective immunity against HIV is likely to lie on the induction of gp120 specific neutralizing antibodies. Marx, "New Hope on the AIDS Vaccine Front", Science, 244:1254 (1989). Potent T cell help might also be critical to promote the generation and the expansion of virus-specific cytotoxic T cells. Reinherz and Schlossman, "The Characterization and Function of Human Immunoregulatory T Lymphocyte Subsets", Immunol. Today, 2:69 (1981); Burns et al, "Thymus Dependence of Viral Antigens", Nature, 256:654 (1975); and Askonas et al., "Cytotoxic T-memory Cells in Virus Infection and the Specificity of Helper T Cells", Immunology, 45:79 (1982). To be durable and broad, protective immunity should rely on induction of immunologic memory to structurally conserved antigenic moieties comprising epitopes displaying limited MHC restriction for T helper cell recognition. Askonas et al. (1982).

Since production of antibodies, including neutralizing antibodies, by B cells is critically dependent on cognate T cell help, and antigenic determinants recognized by T cells are often distinct from the ones recognized by B cells, identification of antigenic moieties recognized by T cells (so-called "T cell epitopes"), is important when considering vaccination strategies based on appropriate combinations of T and B cell epitopes.

It would therefore be useful in the treatment and prevention of AIDS and ARC to have an HIV vaccine capable of producing neutralizing antibodies and concomitantly eliciting T cell help.

Most antigenic determinants recognized by T cells are composed of continuous stretches of peptides. Berkower et al., "Antigen Conformation Determines Processing Requirements for T-cell Activation", Proc. Natl. Acad. Sci. U.S.A., 79:4723 (1982); DeLisi and Berzofsky, "T Cell Antigen Sites Tend to be Amphipathic Structures", Proc. Natl. Acad. Sci. U.S.A., 82:7048 (1985); and Margalit et al., "Prediction of Immunodominant Helper T Cell Antigenic Sites From Primary Sequence", J. Immunol., 138:2213 (1987). B and T cell recognition sites are often located in different regions of a complex antigen. Milich et al., "Nonoverlapping T and B Cell Determinants on an Hepatitis B Antigert pre-S(2) Region Synthetic Peptide", J. Exp. Med., 164:532 (1986). Within the functional T cell repertoire, T helper cells, T cytotoxic cells, and T suppressor cells, appear to recognize structurally distinct determinants. Krzych et al., "Induction of Helper and Suppressor T Cells by Nonoverlapping Determinants on the Large Protein Antigen, β-galactosidase", FASEB J., 2:141 (1988). This functional separation may have important bearing on the development of vaccines, since particular determinants recognized by T suppressor cells may be ablated resulting in important benefits for immunogenicity.

AIDS and ARC are associated with progressive impairment of CD4+ T cells, and increased susceptibility to opportunistic infections. In this respect, HIV-infected persons show decreased T helper cell activity for polyclonal B cell differentiation and decreased T cell proliferative responses to antigens and mitogens associated with an early loss of CD29+ memory T cells. Terpstra et al., "Longitudinal Study of Leukocyte Functions in Homosexual Men Seroconverted for HIV: Rapid and Persistent Loss of B Cell Function After HIV Infection", Eur. J. Immunol., 19:667 (1989); Fahey et al., "Quantitative Changes in T Helper or Suppressor/Cytotoxic Lymphocyte Subsets that Distinguish Acquired Immune Deficiency Syndrome From Other Immune Subsets Disorders", JAMA, 76:95 (1984); Shearer et al., "Functional T Lymphocyte Immune Deficiency in a Population of Homosexual Men Who do not Exhibit Symptoms of Acquired Immune Deficiency Syndrome", J. Clin. Invest., 74:496–506 (1984); Giorgi et al., "Early Effects of HIV on CD4 Lymphocytes in vivo", J. Immunol., 138:3725 (1987); and van Noesel et al., "Functional and Phenotypic Evidence for a Selective Loss of Memory T Cells in Asymptomatic Human Immunodeficiency Virus-infected Men", 86:293 (1990).

The use of synthetic peptides as artificial T cell recognition sites in the composition of candidate subunit vaccines, offers attractive prospects. In this regard, the possibility to educate T helper cells with synthetic peptides for the development of subsequent antibody responses against overlapping and non-overlapping B cell (antibody) recognition sites has been documented in several experimental systems. Berkower et al. (1982); DeLisi and Berzovsky (1985); and Milich et al., "A Single 10-residue PreS(1) Peptide Can Prime T Cell Help for Antibody Production to Multiple Epitopes Within the pre-S(1), pre-S(2), and S regions of HBsAg", J. Immunol., 138:4457 (1987). It has now been found that peptides derived from two regions of the HIV genome elicit T cell activation. These peptides are also capable of inducing the production of neutralizing antibodies to HIV-1.

SUMMARY OF THE INVENTION

In accordance with the present invention, novel peptides corresponding to epitopes of HIV-1 gp120 protein and analogues and homologs thereof are provided. These peptides can be utilized alone or in combination, uncoupled or coupled to other molecules or substrates. The peptides are useful in eliciting T cell activation, immunization against HIV infection, induction of a heightened immune response to HIV and in production of polyclonal and monoclonal antibodies.

Forty synthetic peptides corresponding to the entire primary sequence of the envelope gp120 of the human immunodeficiency virus type 1 (HIV-1) were examined for their ability to induce antibody formation and/or T cell activation. Antibody formation was determined by measuring the amount of peptide-specific antibody formed. T cell activation was measured by the ability of the peptides to induce in vitro proliferative responses and/or IL-2 production when added to cultures of unfractionated, T cell enriched, and/or CD4+ T cell enriched peripheral blood mononuclear cells (PBMC) from immune monkeys. Among four major areas of T cell recognition identified, two novel T cell activating regions were identified, both of which were also found to be capable of inducing, in vivo, the production of neutralizing antibodies to HIV-1. One of these two novel areas corresponds to a highly conserved region of HIV-1 gp-120, the other area being located to a variable region of gp-120. Recognition of the latter variable region does not appear to be restricted by MHC polymorphism, since all of six monkeys immunized with corresponding peptides were found to display in vitro proliferative responses to these peptides. The results of peptides thus have great utility for the development of synthetic subunit AIDS vaccines.

BRIEF DESCRIPTION OF THE DRAWINGS

FIG. 1 is a graph depicting in vitro proliferative responses of monkey peripheral blood mononuclear cells (PBMC) to recall peptide after two and/or three peptide immunizations.

FIG. 2 is a graph depicting in vitro proliferative responses of monkey PBMC to half-overlapping peptides.

DETAILED DESCRIPTION OF THE INVENTION

A vaccine against AIDS, if an efficient one is to be found, is likely to contain components that are capable of inducing T helper cell activity to cognate B cells committed to the production of HIV neutralizing antibodies.

The present invention provides peptides, some of which have previously been found to elicit production of HIV neutralizing antibodies by primate subjects and all of which have now been found to have the surprising property of eliciting T cell activation. The peptides correspond to regions of the gp120 protein with amino acid coordinates as defined by Kennedy et al. (1986). The peptides of the present invention are termed gp120-11 (amino acid coordinates 141–164), gp120-12 (amino acid coordinates 151–176), gp120-13 (amino acid coordinates 164–192), gp120-16 (amino acid coordinates 205–230) and gp120-19 (amino acid coordinates 247–269), gp120-29 (amino acid coordinates 366–389) and gp120-30 (amino acid coordinates 377–400). The peptides of the present invention have been described for use as immunogens in vaccine compositions and to elicit polyclonal or monoclonal antibody productions in U.S. patent application Ser. No. 07/589,422 filed Sep. 27, 1990 which is incorporated herein by reference.

Four topographically related groups of peptides derived from gp120 have now been identified which display T cell activating properties. Two of the gp120 regions found to elicit T cell activation are similar to previously identified T cell epitopes. Bolognesi, "HIV Antibodies and AIDS Design", AIDS 3:S111–S118 (1989). The present study indicates that recognition of the area defined by amino acid coordinates 295–343 by immune T cells may be submitted to strong MHC-restriction as one of the 2 monkeys injected with peptide gp120-25 failed to respond to that particular peptide in vitro. The T cell antigenic determinants in this area seem to be more or less exclusively located within each of the immunizing peptides as none of the overlapping peptides gave rise to in vitro proliferative responses. However, PBMC isolated from monkeys immunized with peptide gp120-24 secreted IL-2 when cultured in the presence of peptide gp120-25, indicating the existence of a minor epitope shared by these two peptides.

The region of gp120 corresponding to amino acid coordinates 295 to 343 (peptides gp120-23, gp120-24 and gp120-25), is similar to a region (amino acid coordinates 301 to 338) which has previously been shown by other investigators to contain a major T cell recognition site (amino acid coordinates 303–337) whose sequence encompasses that of the neutralizing loop. Bolognesi (1989); Javaherian et al., Broadly Neutralizing Antibodies Elicited by the Hypervariable Determinant of HIV-I", Science, 250:1590–1593 (1990); and Rusche et al., "Antibodies That Inhibit Fusion of Human Immunodeficiency Virus infected Cells Bind a 24-amino Acid Sequence of the Viral Envelope, gp120", Proc. Natl. Acad. Sci. U.S.A., 85:3198 (1988).

The area of gp-120 located between amino acid coordinates 409 and 453 (peptides gp120-33, gp120-34 and gp120-35), as described in the Examples presented below, was found to have potent T cell activating properties. The area between amino acid coordinates 409 and 453 has previously been shown to accommodate T cell activating domains. Bolognesi (1989). In this area, two T cell epitopes have been identified, one between amino acid coordinates 410 and 429, and one between amino acid coordinates 428 and 443. The latter area largely overlaps with the CD4-binding site (amino acid coordinates 420–463) of gp120, the main site of virus attachment on permissive T cells. However, only peptide gp120-34, corresponding to amino acids 417–444, induced T cell activation in cultures of PBMC from monkeys immunized with cognate and overlapping peptides. This peptide seems to contain at least two distinct epitopes, one shared with peptide gp120-33 and one shared with peptide gp120-35.

Several other epitopes with T cell activating properties have now been identified in discrete areas of the gp120 molecule. Thus, peptide gp120-4 (amino acid coordinates 53–74) and peptide gp120-21 (amino acid coordinates 269–295), and at least one of their overlapping peptides, were shown to be capable of inducing T cell responses in vitro. However, both of the monkeys immunized with peptide gp120-21, when retested five months after the last booster dose, had lost their in vitro T cell responsiveness to recall peptide. Thus, not every peptide capable of eliciting T cell activation is suitable for use in treatment and prevention of AIDS.

Surprisingly, peptide gp120-19, has now been shown to have T cell immunogenic properties as defined by in vitro proliferative responses of simian PBMC to cognate peptide. Additionally, PBMC from a monkey immunized with OVA-conjugated peptide gp120-16 has now been found to secrete IL-2 after in vitro exposure to peptide gp120-16. Peptide gp120-16 therefore represents an additional novel T cell epitope.

Two novel areas with in vitro T cell activating properties have now been identified. Peptides gp120-11, gp120-12 and gp120-13, corresponding to amino acid coordinates 141 to 192, induce the most potent in vitro proliferative responses, with SI values exceeding sometimes 20 in cultures of T cells from monkeys immunized with corresponding OVA-conjugated peptides. The fact that six out of six monkeys from an outbred population, responded to peptides gp120-11, gp120-12 and gp120-13 strongly indicates that recognition of this bona fide T cell epitope area by simian T cells is not under strict MHC control. Accordingly, at least three distinct epitopes have now been recognized by immune monkey PBMC, one shared by peptides gp120-11 and gp120-12, one shared by peptides gp120-12 and gp120-13 and one additional epitope within peptide gp120-13. In addition, in vitro proliferative responses to peptides gp120-12 and gp120-13 have now been demonstrated in cultures of CD2+ T cells, and also CD4+ T cells, initiated as late as five months after the second immunization indicating the presence of memory T helper (CD4+) cell activating epitopes in that area.

Another novel area identified in this study, includes peptides gp120-29 and gp120-30 (amino acid coordinates 366 to 400) which induced T cell responses in all of 4 monkeys examined. Recognition of this area by immune T cells appears to be also under limited MHC restriction, or to involve epitope(s) associated with polymorphic MHC determinants. At least two epitopes would be expected within this area as the responses did not always overlap.

Importantly, among the novel T cell activating areas that have now been identified, three peptides were also found to be capable of inducing, in vivo, the production of neutralizing antibodies against HIV-1. Thus, sera obtained from all monkeys immunized with peptide gp120-12, peptide gp120-16 and peptide gp120-19 inhibited in vitro HIV induced p-24 antigen release and syncytia formation by human permissive T cell lines exposed to HIV-1 virions of the corresponding (BRU) isolate. Further, peptide gp120-12 is derived from a partly conserved region of gp120 and is associated with a site recognized by neutralizing antibodies. Peptide gp120-16 represents a highly conserved area of gp120 within all 14 different isolates investigated. The efficiency of the peptides, derived from a conserved region of HIV, at inducing the production of HIV-neutralizing antibodies as well as at triggering a T cell response is noteworthy. Peptides gp120-12 and gp120-16 are thus the preferred embodiments of the present invention.

Less than 10% of HIV infected individuals produce antibodies capable of recognizing peptides gp120-12, gp120-15, gp120-16 and gp120-19. Since antibodies are generated in response to immunization with these peptides it is possible to induce an increase in the repertoire of neutralizing antibody producing B cells in HIV positive individuals.

Proteins contain a number of antigenic determinants or epitopes which are the regions of the proteins comprising the recognition and binding sites for specific antibodies. An epitope contains a sequence of 6 to 8 amino acids. Epitopes can be either continuous wherein the sequence of 6–8 amino acids are linear or discontinuous in which case the amino acids are brought together by the three dimensional folding of the protein. Even though an epitope constitutes only a relatively few amino acids, its reactivity with an antibody may be influenced by the amino acids in the protein which surround the epitope.

Studies aimed at mapping antigenic sites or epitopes of proteins have been aided by the use of synthetic peptides corresponding to various regions of the proteins of interest. Lerner et al., in, The Biology of Immunological Disease: A Hospital Practice Book, (Dixon and Fisher, eds.) pp. 331–338 (1983); and Lerner, Adv. Immunol., 36:1 (1984). In addition to their usefulness in epitope mapping studies, synthetic peptides, if encompassing major antigenic determinants of a protein, have potential as vaccines and diagnostic reagents. Van Regenmortel, Ann. Inst. Pasteur Virol., 137E:497–528 (1986); and Van Regenmortel, Laboratory Techniques in Biochemistry and Molecular Biology, Buroden and Van Knippenburg eds. Vol. 19, Synthetic Peptides as Antigens, Elsevier ISBN 0-444-80974-0 (1988).

Synthetic peptides have several advantages with regard to specific antibody production and reactivity. The exact sequence of the synthesized peptide can be selected from the amino acid sequence of the protein as determined by amino acid sequencing of the protein or the predicted amino acid sequence determined from the DNA sequence encoding the protein. The use of specific synthetic peptides eliminates the need for the full-length protein in vaccination and the production of or assay for antibodies. Furthermore, the solid phase peptide synthetic techniques of Merrifield and coworkers allow for essentially unlimited quantities of the synthesized peptide of interest to be chemically produced. Erickson and Merrifield in The Proteins, 3rd Edit., Vol. 2, Academic Press, New York, Chapter 3 (1976). The availability of automated peptide synthesizers has further advanced such techniques.

Although a variety of criteria can be used to predict antigenic regions of proteins, peptides corresponding to such regions may not always be useful as vaccines. For example, antigenicity may be lost because the peptide is not in the proper spatial orientation to be recognized by antibodies which react with the protein. It has also been found that certain peptides derived from type C retroviruses and HIV act as immune-suppressive agents much as does HIV itself. Cianciolo et al., J. Immunol., 124:2900–2905 (1980); and Cianciolo et al., Nature 230:453–455 (1985). Peptides such as these, which have a deleterious effect on the patient, would not be suitable for use as vaccines.

Furthermore, as is particularly evident with HIV-1 and HIV-2, there is significant genetic variability within each of these two virus groups leading to many serotypes, or isolates, of the viruses. This has put a significant constraint on choosing a region of a protein from which to derive a peptide for use in formulating immunogens. However, certain immunodominant portions of HIV-1 and HIV-2 proteins have been found to be relatively invariant. Synthetic peptides may also be key to viral vaccines in that they may induce an immune response against type common sequences not normally immunogenic in the native molecule. These otherwise silent epitopes may be of broad protective specificity. Steward et al., Immunol. Today, 8:51–58 (1987). Several experimental vaccines have been formulated with the aim of preventing infection in those people who are likely to be exposed to the virus. Berman et al., "Protection of Chimpanzees from Infection by HIV-1 After Vaccination With Recombinant Glycoprotein gp120 but Not gp160", Nature 345:622–625 (1990).

A number of neutralization epitopes on gp120 have been found and defined by several investigators, for an overview see Bolognesi, AIDS (1989) 3(suppl 1):S111–S118. In his overview Bolognesi refers to four different virus neutralization epitopes with the following amino acid coordinates: 254–274, 303–337, 458–484 and 491–523. The peptide with amino acid coordinates 254–274 was used to immunize rabbits and the resulting antiserum was found to neutralize HIV-1 as described above. Hoet al., Science, 239:1021–1023 (1988).

The peptides encompassed by the invention comprise amino acid sequences each containing at least one continuous (linear) epitope that elicits production of activated T cells in the host in addition to eliciting the production of HIV specific antibodies.

The invention thus encompasses immunogenic peptides corresponding to regions of HIV gp120 protein encoded by the envelope gene of HIV-1 HTLV III-B described by Muesing et al., "Nucleic Acid Structure and Expression of the Human AIDS/Lymphadenopathy Retrovirus", Nature, 313:450–458 (1985). The nucleotide sequence is given in Genbank Release 63 under the name HIVPV22. The invention further encompasses functionally equivalent variants of the peptides which do not significantly affect the immunogenic properties of the peptides. For instance, conservative substitution of amino acid residues, one or a few amino acid deletions or additions, and substitution of amino acid residues by amino acid analogues are within the scope of the invention.

Homologs are peptides which have conservatively substituted amino acid residues and peptides derived from corresponding regions of different HIV isolates. Amino acids which can be conservatively substituted for one another include but are not limited to: glycine/alanine; valine/isoleucine/leucine; asparagine/glutamine; aspattic acid/glutamic acid; serine/threonine; lysine/arginine; and phenylalanine/tyrosine. Homologous peptides are considered to be within the scope of the invention if they are recognized by antibodies which recognize the peptides designated gp120-12, gp120-16 and gp120-19 the sequences of which are shown below. Further, all homologous peptides corresponding to the peptides of the present invention but derived from different HIV isolates are also encompassed by the scope of this invention.

The invention also encompasses polymers of one or more of the peptides, and peptide analogues or homologs are within the scope of the invention. Also within the scope of this invention are peptides of fewer amino acid residues than the peptides but which encompass one or more immunogenic epitopes present in any one of the peptides and thus retain the immunogenic properties of the base peptide.

The invention further encompasses functionally equivalent variants of the peptides which do not significantly affect the antigenic or T cell activating properties of the peptides. For instance, various analogues, or peptidomimetics, are known in the art and can be used to replace one or more of the amino acids in the peptides. Analogues are defined as peptides which are functionally equivalent to the peptides of the present invention but which contain certain non-naturally occurring or modified amino acid residues. Additionally, polymers of one or more of the peptides are within the scope of the invention.

The use of peptide analogues can result in peptides with increased activity, that are less sensitive to enzymatic degradation, and which are more selective. A suitable proline analogue is 2-aminocyclopentane carboxylic acid ($\beta Ac^5 c$) which has been shown to increase activity of a native peptide more than 20 times. Mierke et al., "Morphiceptin Analogs Containing 2-aminocyclopentane Carboxylic Acid as a Peptidomimetic for Proline", Int. J. Peptide Protein Res., 35:35–45 (1990). See also Portoghese et al., "Design of Peptidomimetic S Opioid Receptor Antagonists Using the Message-Address Concept", J. Med. Chem., 33:1714–1720 (1990); and Goodman et al., "Peptidomimetics: Synthesis, Spectroscopy, and Computer Simulations", Biopolymers, 26:S25–S32 (1987).

The peptides were synthesized by known solid phase peptide synthesis techniques. Barany and Merrifield, The Peptides: Analysis, Synthesis, Biology, Vol. 1, Gross and Meinenhofer, eds., Academic Press, New York, Chap. 1 (1980). The synthesis also allows for one or more amino acids not corresponding to the original protein sequence to be added to the amino or carboxyl terminus of the peptide. Such extra amino acids are useful for coupling the peptides to another peptide, to a large carrier protein or to a solid support. Amino acids that are useful for these purposes include but are not limited to tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptides to another protein or peptide molecule or a support. Procedures for coupling peptides to each other, carrier proteins and solid supports are well known in the art. Peptides containing the above-mentioned extra amino acid residues either carboxy or amino terminally, uncoupled or coupled to a carrier or solid support are consequently within the scope of the invention. Reference to the peptides of the present invention encompasses all of the embodiments discussed herein.

An alternative method of vaccine production is to use molecular biology techniques to produce a fusion protein containing one or more of the peptides of the present invention and a highly immunogenic protein. For instance, fusion proteins containing the antigen of interest and the B subunit of cholera toxin have been shown to induce an immune response to the antigen of interest. Sanchez et al., "Recombinant System For Overexpression of Cholera Toxin B Subunit in *Vibrio cholerae* as a Basis for Vaccine Development", Proc. Natl. Acad. Sci. U.S.A., 86:481–485 (1989). It is thus implicit in the present invention that vaccine constructs based on appropriate constructions of B and T cell epitopes fused to a carrier protein like cholera toxin would represent important benefits in vaccination.

The novel peptide amino acid sequences are set forth below and in Table 2. The amino acid residues are derived from the nucleotide sequence previously described by Kennedy et al. (1986). The peptides may contain either an amido or carboxy group at their carboxy termini.

gp120-11
X—Ser—Ser—Ser—Gly—Arg—Met—Ile—Met—Glu—Lys—Gly—Glu—Ile—Lys—
Asn—Cys—Ser—Phe—Asn—Ile—Ser—Thr—Ser—Y—Z gp120-12
X—Gly—Glu—Ile—Lys—Asn—Cys—Ser—Phe—Asn—Ile—Ser—Thr—
Ser—Ile—Arg—Gly—Lys—Val—Gln—Lys—Glu—Tyr—Ala—Phe—Phe—Y—Z gp120-13
X—Ile—Arg—Gly—Lys—Val—Gln—Lys—Glu—Tyr—Ala—Phe—Phe—Tyr—Lys—
Leu—Asp—Ile—Ile—Pro—Ile—Asp—Asn—Asp—Thr—Thr—Ser—Tyr—Thr—Y—Z gp120-16
X—Pro—Lys—Val—Ser—Phe—Glu—Pro—Ile—Pro—Ile—His—Tyr—Cys—
Ala—Pro—Ala—Gly—Phe—Ala—Ile—Leu—Lys—Cys—Asn—Asn—Y—Z gp120-19
X—Thr—His—Gly—Ile—Arg—Pro—Val—Val—Ser—Thr—Gln—Leu—
Leu—Leu—Asn—Gly—Ser—Leu—Ala—Glu—Glu—Glu—Y—Z gp120-29
X—Gly—Asp—Pro—Glu—Ile—Val—Thr—His—Ser—Phe—Asn—Cys—Gly—Gly—
Glu—Phe—Phe—Tyr—Cys—Asn—Ser—Thr—Gln—Y—Z gp120-30
X—Cys—Gly—Gly—Glu—Phe—Phe—Tyr—Cys—Asn—Ser—Thr—Gln—Leu—Phe—
Asn—Ser—Thr—Trp—Phe—Asn—Ser—Thr—Trp—Y—Z wherein X is either a hydrogen atom of the amino terminal $NH_2$ group of the peptide or an additional amino acid being selected to facilitate coupling of the peptide to a carrier; Y is absent or Cys; and Z is the carboxyl group of the carboxy terminal amino acid or an amido group. The amino acid abbreviations used are defined in Table 2.

In addition to eliciting T cell activation, several of the peptides are useful as vaccines to protect against future infection by HIV or to heighten the immune response to HIV in subjects already infected by HIV. Although any human subject could be vaccinated with the peptides, the most suitable subjects are people at risk for HIV infection. Such subjects include but are not limited to homosexuals, prostitutes, intravenous drug users, hemophiliacs and those in the medical professions who have contact with patients or biological samples. The invention also provides monoclonal and polyclonal antibodies which specifically recognize the peptides. The invention further provides antibodies produced in response to vaccination with the peptides which neutralize HIV.

In the preferred embodiment of the present invention, the peptides are formulated into compositions for use as immunogens. These immunogens can be used as vaccines in mammals including humans or to elicit T cell activation and/or production of polyclonal and monoclonal antibodies in animals. For formulation of such compositions, an amount sufficient to elicit T cell activation of at least one of the peptides (about 1–500 μg) is admixed with a physiologically acceptable carrier suitable for administration to mammals including humans.

The peptides may be covalently attached to each other, to other peptides, to a protein carrier or to other carriers, incorporated into liposomes or other such vesicles, and/or mixed with an adjuvant or adsorbent as is known in the vaccine art. For instance, the peptide or peptides can be mixed with immunostimulating complexes as described by Takahashi et al., "Induction of CD8+ Cytotoxic T Cells by Immunization With Purified HIV-1 Envelope Protein and ISCOMS", Nature, 344:873–875 (1990). Alternatively, the peptides are uncoupled and merely admixed with a physiologically acceptable carrier such as normal saline or a buffering compound suitable for administration to mammals including humans.

As with all immunogenic compositions for eliciting antibodies, the immunogenically effective amounts of the peptides of the invention must be determined empirically. Factors to be considered include the immunogenicity of the native peptide, whether or not the peptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

The invention is further illustrated by the following specific examples which are not intended in any way to limit the scope of the invention. In order to determine T cell activation, PBMC from monkeys immunized with OVA-conjugated HIV gp120 peptides were tested for their ability to produce IL-2 and/or to proliferate when exposed in vitro to recall (immunizing), overlapping, and non overlapping peptide(s).

EXAMPLE 1

Animals Used in Subsequent Examples

Cynomolgus monkeys (MaCaca fascicularis) were given 3 intramuscular doses of ovalbumin (OVA)-conjugated peptides (see below), three weeks apart, each dose consisting of 100 μg of ovalbumin-coupled peptide emulsified in Freund's complete (first dose) or incomplete (booster doses) adjuvant.

EXAMPLE 2

Peptide Synthesis

40 HIV-1 gp120 peptides (Table 1), with an additional carboxy-terminal cysteine residue, were synthesized on solid phase with an Applied Biosystems 430A peptide synthesizer (Applied Biosystems, Foster City, Calif., U.S.A.) using the polymer p-methylbenzhydryl amine resin as solid phase (Peptides Int., Louisville, U.S.A.).

All amino acids for use in synthesis contained t-butylcarbonyl groups (t-Boc) protecting the $\alpha$—$NH_2$ group and were obtained from Novabiochem AG, Switzerland. Amino acids with reactive side chain groups contained additional protective groups to prevent unwanted and undesirable side chain reactions. The individual protected amino acids used in synthesizing all of the peptides are set forth in Table 1.

TABLE 1

| AMINO ACIDS USED IN PEPTIDES SYNTHESIS |
|---|
| Boc-Ala-OH |
| Boc-Arg (Tos)-OH |
| Boc-Asn-OH |
| Boc-Asp (Obzl)-OH |
| Boc-Cys (Pmeobzl)-Oh |
| Boc-Glu (Obzl)-OH |
| Boc-Gln-OH |
| Boc-Gly-OH |
| Boc-His-(Tos)-OH |
| Boc-Ile-OH ½$H_2O$ |
| Boc-Leu-OH $H_2O$ |
| Boc-Lys (2-CI-Z)-OH (cryst.) |
| Boc-Met-OH |
| Boc-Phe-OH |
| Boc-Pro-OH |
| Boc-Ser (Bzl)-OH DCHA |
| Boc-Thr (Bzl)-OH |
| Boc-Trp (Formyl)-OH |
| Boc-Tyr (2-Br-Z)-OH |
| Boc-Val-OH |

Tos: Tosyl or p-Toluene sulfonic acid
Obzl = Benzyloxy
Pmeobzl = p-Methylbenzyloxy
2-CL-Z = Carbobenzoxy chloride
2-Br-Z = Carbobenzoxy bromide The peptides were synthesized using the t-Boc synthesis protocol as suggested by the manufacturer. All solvents were from Applied Biosystems and the side chain protected amino acids used were from Nova Biochem (Switzerland) and Applied Biosystems. Following each amino acid coupling, a sample was taken and a quantitative ninhydrin assay was performed. Only if the coupling efficiency exceeded 99% for each amino acid coupled was the peptide accepted for further processing. Completed peptides were cleaved from the solid phase and amino acid side chains were deprotected by acidic hydrolysis using anisole and ethanedithiol (Merck, Germany) as scavengers.

After completion of a particular synthesis, the protecting groups were removed from the synthesized peptide and the peptide was cleaved from the solid support resin by treatment with trifluoromethane sulfonic acid (TFMSA) according to the method described by Bergot et al., "Utility of Trifluoromethane Sulfonic Acid as a Cleavage Reagent in Solid Phase Peptide Synthesis", Applied Biosystems User Bulletin, Peptide Synthesizer, Issue No. 16, Sept. 2, 1986. The following is the detailed protocol used.

1. For 1 gram peptide-resin, 3 ml Thio-Anisol 1,2-Ethane-Dithiol (2:1) was added as scavenging agent and the mixture was incubated with continuous stirring for 10 min. at room temperature.

2. Trifluoracetic Acid (TFA), 10 ml, was added and stirred continuously for 10 min. at room temperature.

3. TFMSA, 1 ml, was added dropwise with forceful stirring and reacted for 25 min. at room temperature.

4. Following cleavage, the peptides were precipitated with and washed with anhydrous ether.

5. The precipitated and washed peptides were dissolved in a small volume of TFA.

6. The dissolved peptides were again precipitated and washed as above in step 4 and the precipitate was dried under a stream of $N_2$.

Prior to use in specific assays, the peptides can be further purified, if desired, by reverse phase high performance liquid chromatography (HPLC). A particularly suitable column for such purification is the reverse-phase Vydak® C-18 column using a water (TFA) - acetonitrile (TFA) gradient to elute the peptides. Forty peptides were synthesized having the amino acid sequences shown in Table 2.

The amino acid sequences of the peptides, 17-29 amino acids long, half overlapping each other and entirely encompassing gp-120, were obtained from the HIV-1 BRU isolate. Muesing et al., (1985).

TABLE 2

| Peptide | Amino Acid Coordinates** | Amino Acid Sequence* |
|---|---|---|
| gp120-1 | 1–28 | MRVKEKYQHLWRWGTMLGMLMIC |
| gp120-2 | 22–46 | GMLMICSATEKLWVTVYYGVPVWK |
| gp120-3 | 40–64 | GVPVWKEATTTLFCASDAKAYDTE |
| gp120-4 | 53–74 | CASDAKAYDTEVHNVWATHAC |
| gp120-5 | 64–89 | VHNVWATHACVPTDPNPQEVVLVNV |
| gp120-6 | 74–100 | VPTDPNPQEVVLVNVTENFNMWKNDM |
| gp120-7 | 89–116 | TENFNMWKNDMVEQMHEDIISLWDQSL |
| gp120-8 | 100–126 | VEQMHEDIISLWDQSLKPCVKLTPLC |
| gp120-9 | 116–141 | KPCVKLTPLCVSLKCTDLKNDTNTN |
| gp120-10 | 126–151 | VSLKCTDLKNDTNTNSSSGRMIMEK |
| gp120-11 | 141–164 | SSSGRMIMEKGEIKNCSFNISTS |
| gp120-12 | 151–176 | GEIKNCSFNISTSIRGKVQKEYAFF |
| gp120-13 | 164–192 | IRGKVQKEYAFFYKLDIIPIDNDTTSYT |
| gp120-14 | 176–205 | YKLDIIPIDNDTTSYTLTSCNTSVITQAC |
| gp120-15 | 192–218 | LTSCNTSVITQACPKVSFEPIPIHYC |
| gp120-16 | 205–230 | PKVSFEPIPIHYCAPAGFAILKCNN |
| gp120-17 | 218–247 | APAGFAILKCNNKTFNGTGPCTNVSTVQC |
| gp120-18 | 230–257 | KTFNGTGPCTNVSTVQCTHGIRPVVST |
| gp120-19 | 247–269 | THGIRPVVSTQLLLNGSLAEEE |
| gp120-20 | 257–282 | QLLLNGSLAEEEVVIRSANFTDNAK |
| gp120-21 | 269–295 | VVIRSANFTDNAKTIIVQLNQSVEIN |
| gp120-22 | 282–306 | TIIVQLNQSVEINCTRPNNNTRKS |
| gp120-23 | 295–320 | CTRPNNNTRKSIRIQRGPGRAFVTI |
| gp120-24 | 306–326 | IRIQRGPGRAFVTIGKIGNMRQAH |
| gp120-25 | 320–343 | GKIGNMRQAHKNISRAKWNNTLK |
| gp120-26 | 326–353 | KNISRAKWNNTLKQIDSKLREQF |
| gp120-27 | 343–366 | QIDSKLREQFGNNKTIIFKQSSG |
| gp120-28 | 353–377 | GNNKTIIFKQSSGGDPEIVTHSFN |
| gp120-29 | 366–389 | GDPEIVTHSFNCGGEFFYCNSTQ |
| gp120-30 | 377–400 | CGGEFFYCNSTQLFNSTWFNSTW |
| gp120-31 | 389–409 | LFNSTWFNSTWSTEGSNNTE |
| gp120-32 | 400–417 | STEGSNNTEGSDTITLP |
| gp120-33 | 409–429 | GSDTITLPCRIKQFINMWQE |
| gp120-34 | 417–444 | CRIKQFINMWQEVGKAMYAPPISGQIR |
| gp120-35 | 429–453 | VGKAMYAPPISGQIRCSSNITGLL |
| gp120-36 | 444–466 | CSSNITGLLLTRDGGNNNNESE |
| gp120-37 | 453–476 | LTRDGGNNNNESEIFRPGGGDMR |
| gp120-38 | 466–488 | IFRPGGGDMRDNWRSELYKYKV |
| gp120-39 | 476–497 | DNWRSELYKYKVVKIEPLGVA |
| gp120-40 | 488–511 | VKIEPLGVAPTKAKRRVVQREKR |

*Amino acid abbreviations

| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

**As previously described by Kennedy et al. (1986).

EXAMPLE 3

Preparation of Peptides for Immunization

Peptides according to the present invention were covalently coupled to ovalbumin grade V (Sigma, St. Louis, Mo., U.S.A.) at an approximate 10:1 (peptide:ovalbumin) molar ratio using N-succinimidyl 3-(2-pyridyldithio) propionate (SPDP), (Pharmacia, Uppsala, Sweden) as bifunctional linker according to the manufacturer's instructions (Pharmacia) i.e. briefly as follows:

Ovalbumin was dissolved in coupling buffer (0.2M $NaH_2PO_4$, Ph 8.5). The dissolved ovalbumin was then run through a Sephadex G-25M column (Pharmacia, Sweden), using the same buffer. Protein concentration was measured at 280 nm and the recovery was determined. SPDP was dissolved in 99.5% ethanol to a final concentration of 40 mM. SPDP was then added dropwise to the ovalbumin solution under stirring. The SPDP-ovalbumin mixture was then left at room temperature for approximately 30 minutes. The ovalbumin-SPDP conjugate was separated from unconjugated SPDP by running the mixture through a Sephadex G-25M column, using water as eluent. The degree of substitution for the ovalbumin-SPDP conjugate was determined after diluting 50 µl conjugate in 2 ml of water, by measuring the diluted conjugate at 280 nm and the diluted conjugate plus 100 µl Dithiothreitol (DTT) (Sigma) at 343 nm, in order to determine the amount to be added to the peptide solution.

Finally, the synthetic peptide to be coupled to the ovalbumin-SPDP conjugate was dissolved in 10% acetic acid to a final concentration of 1 mg/ml and a suitable amount of ovalbumin-SPDP conjugate (as determined by the substitution degree above) was added and allowed to stand overnight at room temperature.

EXAMPLE 4

Immunization Protocols

*M. fascicularis* were used to generate antibodies. Prior to the initial peptide injection, a blood sample was drawn from the monkeys. This initial blood sample is termed "pre-immune" (Tables 5–8) and is used as an internal control and analyzed simultaneously with respective immuneserum.

The monkeys were injected with 100 µg peptide-SPDP-ovalbumin suspended in 0.5 ml phosphate buffered saline (PBS). The monkeys were immunized intramuscularly three times, three weeks apart. As adjuvant, 0.5 ml of Freund's complete adjuvant was used for all initial immunizations and Freund's incomplete adjuvant was used for booster shots. Two weeks after the final immunization the monkeys were bled by removing a 10 ml blood sample from the fossa and pre-immune and hyperimmune sera were subject to neutralization assays as described in Example 9.

EXAMPLE 5

Isolation and Fractionation of Lymphocytes from Immunized *M. fascicularis*

Heparinized venous blood was collected from the femoral vein, at least two weeks after the second and/or the third injections. Peripheral blood mononuclear cells (PBMC) were obtained by gelatin sedimentation followed by density gradient centrifugation by the following method. A solution of 3% (weight/volume) gelatin (gelatin L936, PB Gelatins UK LTD, GB) in Hank's Balanced Salt Solution was mixed with the blood at a 1:3 ratio and erythrocytes were allowed to sediment for one hour at 37° C. The erythrocyte-free supernatant was layered onto a Ficoll-Hypaque cushion (Pharmacia, Sweden) and centrifuged for 15 minutes at 930 xg, at 20° C. Interface PBMC were washed twice by centrifugation (500 xg, 20° C., 5 min) with isotonic phosphate-buffered saline (PBS, 0.01M phosphate buffer in 0.15M NaCl, pH 7.4).

In some examples represented below, T cells were enriched by rosetting with AET-treated sheep red blood cells as described by Kaplan and Clarc, "Improved Rosetting Assay for Detection of Human T Lymphocytes", J. Immunol. Met., 6:131 (1974) followed by density centrifugation on Ficoll-Hypaque. The rosetted cells (nominal T cells) were collected from the pellets and resuspended for 20 seconds with distilled water to lyse sheep red blood cells. Further enrichment into CD4+ T cells was obtained by paramagnetic depletion of CD8+ T cells using microspheres coated with monoclonal anti-CD8 antibodies (Dynal AS, Norway), according to the manufacturer's instructions.

EXAMPLE 6

Lymphocyte Proliferation Assays

Unfractionated PBMC were resuspended in complete medium (see below) and dispersed in round-bottomed 96 micro-well plates (Nunc, Denmark) at three different cell densities ($2 \times 10^5$, $1 \times 10^5$ and $5 \times 10^4$ cells per well) in Iscove's medium supplemented with 10% fetal calf serum (FCS, Biological Industries, Israel), 3 µg/ml L-Glutamine (Gibco, UK) and 0.1 mg/ml Gentamycin-sulfate (Essex Lakemedel AB, Sweden). Fractionated T cells ($2 \times 10^5$ or $1.2 \times 10^5$ nominal T cells, or $4 \times 10^4$ CD4+ T cells) were dispersed in separate sets of wells together with $4 \times 10^4$ or $2 \times 10^4$ autologous T cell-depleted irradiated (2500 rad), PBMC as a source of accessory cells. Synthetic peptides were dissolved in dimethylsulfoxide (20 µg/ml) and further diluted in culture medium. Uncoupled peptides were added at different concentrations (10, 1 and 0.1 µg/ml) to the culture wells.

Concanavalin A (Sigma) (10 µg/ml) was added to separate cultures as a positive control. Cells, in a final volume of 0.2 ml, were incubated for five days at 37° C. in a humid atmosphere with 7.5% $CO_2$. After four days, 25 µl of culture supernatant were collected from each well and frozen at −70° C. until assayed for IL-2 activity according to the method described in example 5. 16 hours prior to the completion of the culture period, 20 µl culture medium containing 1 µCi of [$^3$H]thymidine (Amersham, UK) were added to each well. The harvesting and subsequent measurement of incorporated radioactivity was performed on an automated filter cell harvester coupled to an argon activated β-scintillation counter (Inotech, Switzerland). Data were expressed as arithmetic mean stimulating indexes (SI), the latter SI being defined as the mean ratio of [$^3$H]-thymidine incorporated in peptide stimulated cultures (mean from three cultures) divided by corresponding triplicate of control cultures (unstimulated). A mean SI of at least 2 is considered positive.

As seen in FIG. 1, a substantial number (14/40) of peptides that were injected into monkeys in an OVA-substituted form, induced in vitro proliferation of PBMC from corresponding immune animals. In FIG. 1, results are expressed as mean SI±SD of triplicate cultures (if tested on two monkeys). Black bars indicate a positive result. The frequency of responding monkey(s) is indicated. Four major areas corresponding to the additive sequence of 2 to 3 overlapping peptides were found to accommodate this activity. Peptides gp120-11, gp120-12 and gp120-13 (amino acid coordinates 141-192) correspond to one such area. All six monkeys immunized with one of these three peptides responded to recall peptide. Another major area comprises peptides gp120-23, gp120-24 and gp120-25 (amino acid coordinates 295-343) which induced proliferative responses of PBMC from at least one out of 2 monkeys immunized with the corresponding peptide. A third area, comprising peptides gp120-29 and gp120-30, accommodates a site(s) of proliferation inducing activity on PBMC from monkeys immunized with the corresponding OVA-conjugated peptides. The fourth area consists of peptides gp120-33, gp120-34 and gp120-35 (amino acid coordinates 409-453) where each peptide could induce proliferation of PBMC from at least one (peptides gp120-33 and gp120-35) or both of 2 (peptide gp120-34) immunized monkeys.

Apart from these major areas, three discrete peptides, i.e. peptides gp120-4 (amino acid coordinates 53-74), gp120-19 and gp120-21 (amino acid coordinates 269-295), were shown to induce in vitro proliferative responses when added to PBMC from monkeys immunized with the corresponding OVA-conjugated peptide.

Peptides found to be capable of inducing a proliferative response of PBMC from monkeys immunized with the corresponding OVA-coupled peptide were reassayed on PBMC from at least three other monkeys immunized with a non-cognate OVA-coupled peptide. Peptides gp120-4, gp120-13 and gp120-34 induced proliferation of PBMC from 1 out of 3 monkeys and peptide gp120-30 in 1 monkey out of 7 (SI ranging between 2.0 and 2.5) while the other peptides failed to induce any significant proliferative responses.

Peptides capable of inducing a proliferative response in one or two immunized monkeys were retested after the third immunization. On this occasion, the in vitro proliferative responses of PBMC from immune monkeys to each of 2 peptides containing a sequence half overlapping with the immunizing peptide were also evaluated.

As seen in FIG. 2, PBMC from both monkeys immunized with OVA-conjugated peptide gp120-11 responded also in vitro to peptide gp120-12, but none of the peptide gp120-12-immunized monkeys responded to peptide gp120-11. Cells were obtained two weeks after the third immunization. The peptides tested were selected on the basis of in vitro responsiveness to the immunizing peptide after two immunizations. In FIG. 2, results are expressed as mean SI of all triplicates tested % SD (if tested on two monkeys). Black bars indicate a positive result.

Similarly, monkeys immunized with peptide gp120-12 responded to peptide gp120-13 but none of the peptide gp120-13 immunized monkeys responded to peptide gp120-12. In the next area of in vitro proliferative activity, i.e. peptides gp120-23, gp120-24 and gp120-25, none of the overlapping peptides induced in vitro proliferation of PBMC from any of the monkeys immunized with OVA-conjugated peptides. The same holds true for PBMC from monkeys immunized with peptides gp120-29 and gp120-30 (OVA-conjugated) as no response to overlapping peptides is achieved. In the area consisting of peptides gp120-33, gp120-34 and gp120-35, PBMC from the monkey immunized with, and responding to, peptide gp120-33 also proliferated in vitro to peptide gp120-34. PBMC from the other monkeys were negative in this respect. Of the three distinct epitopes identified, only PBMC from the peptide gp120-4 immunized monkey responded in vitro to an overlapping peptide, i.e. to peptide gp120-5.

The proliferative responses of different cell fractions from two monkeys (immunized with peptide gp120-12 or peptide gp120-13) were examined. As seen in Table 3, enrichment of CD2+ T cells increased the proliferative response of PBMC obtained from both monkeys when cultured in the presence of immunized (but uncoupled) peptide. Also, existing responses to overlapping peptides remained relatively constant. After a further depletion of CD8+ T cells, the CD4+ T cell enriched fractions (containing 9 to 18% of the original CD2+ T cell fractions) still proliferated in response to incubation with immunized peptide. However, the CD4+ T cell enriched fraction from the peptide gp120-12 immunized monkey did not proliferate in response to any of the overlapping peptides.

TABLE 3

IN VITRO POLIFERATIVE RESPONSES TO RECALL PEPTIDES OF TOTAL PBMC AS WELL AS CD2+ AND CD4+ ENRICHED FRACTIONS OF CELLS OBTAINED FROM MONKEYS 5 MONTHS AFTER IMMUNIZATION WITH OVA-CONJUGATED PEPTIDES

| Immunized Peptide | In vitro Peptide | Stimulation Index (SI) of | | |
|---|---|---|---|---|
| | | Total PBMC | CD2+ Enriched Fraction | CD4+ Enriched Fraction |
| gp120-12 | gp120-11 | 2.7 | 2.8 | 1.1 |
| | gp120-12 | 2.5 | 8.6 | 2.6 |
| | gp120-13 | 3.9 | 3.6 | 1.4 |
| gp120-13 | gp120-12 | 1.0 | 0.4 | 0.8 |
| | gp120-13 | 2.5 | 2.9 | 5.6 |
| | gp120-14 | 2.1 | 2.4 | 4.0 |

In Table 3, the various columns were obtained as follows. Immunized peptide: 100 µg of OVA-conjugated peptide was immunized at three occasions in Freund's complete (1st dose) or incomplete (boosting doses) adjuvant;

In vitro peptide: unconjugated peptide;

Total PBMC: mean SI of four triplicates of different cell densities and peptide concentrations;

CD2+ enriched fraction: $2 \times 10^5$ SRBC-rosetted PBMC incubated with $4 \times 10^4$ irradiated, non-rosetted cells together with 10 µg/ml of peptide(s):

CD4+ enriched fraction: $1.25 \times 10^5$ (peptide gp120-12 immunized monkey) or $4 \times 10^4$ (peptide gp120-13 immunized monkey) SRBC-rosetted PBMC further enriched in CD4+ T cells by incubating with anti-CD8+ coated beads were incubated with $2 \times 10^4$ irradiated, non-rosetted cells together with 10 µg/ml of peptide(s).

EXAMPLE 7

IL-2 Assay

The IL-2 content of individual cell microcultures was determined by the bioassay performed as described by Gillis et al., "T Cell Growth Factor: Parameters of Production and a Quantitative Microassay for Activity", J. Immunol., 120:2027 (1978). Briefly, supernatants were added at a final dilution of 1:4 to $10^4$ CTLL-2 cells. Cells were incubated for 24 hours at 37° C. in flat-bottomed 96 microwell plates (Nunc, Denmark) in Iscove's medium supplemented with 10% FCS, 3 μg/ml L-Glutamine, 0.1 mg/ml Gentamycinsulfate and $5 \times 10^{-5}$M β-Mercaptoethanol. Six hours prior to completion of the culture period, 1 μCi of [$^3$H]-thymidine was added. The cells were harvested and [$^3$H]-thymidine incorporation was determined as described in Example 6. IL-2 content in the supernatants was determined by extrapolation from a standard dose-response curve generated by culturing CTLL-2 cells in the presence of known amounts of recombinant human IL-2 (Genzyme, Boston, Mass.).

As seen in Table 4, several cell culture supernatants contained detectable amounts of IL-2 in cultures of PBMC from monkeys immunized with OVA-conjugated peptides gp120-11, gp120-12, gp120-13, gp120-16, gp120-21, gp120-25, gp120-30 and gp120-34, secreted IL-2 could be detected after in vitro challenge with the corresponding, unconjugated, peptide. The ratio of secreted IL-2 found after 4 days of in vitro culturing ranged from 0.2 to 1.0 U/ml. Cell culture supernatants of PBMC derived from monkeys immunized with peptides gp120-11, gp120-12, gp120-13, gp120-30 and gp120-34 also contained IL-2 after in vitro exposure to one or two of the overlapping peptides. Accordingly, PBMC from a monkey immunized with peptide gp120-11 secreted detectable levels of IL-2 in the cell supernatant after 4 days of stimulation with peptide gp120-12, and a monkey immunized with peptide gp120-12 secreted detectable levels of IL-2 after stimulation with peptide gp120-13. Cell culture supernatants containing IL-2 were identified from both PBMC cultures containing overlapping peptides (peptides gp120-12 and gp120-14) together with PBMC from a peptide gp120-13 immunized monkey and the same holds true for peptides gp120-33 and gp120-35 when co-cultured with PBMC from a peptide gp120-34 immunized monkey. Finally, PBMC obtained from a peptide gp120-30 immunized monkey secreted detectable amounts of IL-2 not only when cultured in the presence of peptide gp120-30, but also when peptide gp120-29 had been added to the cultures.

TABLE 4

IL-2 CONTENT IN SUPERNATANTS OF PBMC FROM MONKEYS IMMUNIZED WITH OVA-CONJUGATED PEPTIDES AFTER IN VITRO EXPOSURE TO UNCONJUGATED, RECALL PEPTIDE(S).

| Immunized Peptide[a] | In vitro Peptide[b] | IL-2 Content in Culture Supernatants (U/ml)[c] |
|---|---|---|
| gp120-11 | gp120-11 | 0.28 |
|  | gp120-12 | 0.26 |
| gp120-12 | gp120-12 | 0.28 |
|  | gp120-13 | 0.22 |
| gp120-13 | gp120-12 | 0.36 |
|  | gp120-13 | 1.01 |
|  | gp120-14 | 0.61 |
| gp120-16 | gp120-16 | 0.22 |
| gp120-21 | gp120-21 | 0.37 |
| gp120-22 | gp120-3 | 0.20 |
| gp120-24 | gp120-25 | 0.21 |
| gp120-25 | gp120-25 | 0.2 |
| gp120-30 | gp120-29 | 0.23 |
|  | gp120-30 | 0.20 |
| gp120-33 | gp120-34 | 0.53 |
| gp120-34 | gp120-33 | 0.20 |
|  | gp120-34 | 0.27 |
|  | gp120-35 | 0.25 |

[a]OVA-conjugated peptides.
[b]unconjugated peptides
[c]IL-2 content of the highest triplicate from peptide-stimulated PBMC in vitro.

EXAMPLE 8

Cells and Virus Stocks

All neutralization tests were performed using H-9 cells and HTLV-111B virus (originating from R. C. Gallo and supplied by Dr. William Hall, North Shore Hospital, Manhasset, N.Y.). H-9 cells (designated H9 NY) were maintained in RPMI Medium (Gibco) supplemented with 20% fetal calf serum (FCS), penicillin/streptomycin (PEN/STREP 50 μg/ml each and without any fungicides). Cells were subcultured at a dilution of 1:3 every 4 days.

Cells were scraped from the plates and pelleted by centrifugation at 325 x g. Pelleted cells were resuspended in 1 ml of stock virus previously diluted 1/10 and allowed to adsorb for 60 min at 37° C. with frequent stirring. After adsorption of the virus, the cells were recentrifuged and resuspended in 10 ml of RPMI with 20% FCS and polybrene (2 μg/ml) (giving a final concentration of $5 \times 10^5$ cells/ml) and incubated at 37° C. in 5% $CO_2$.

Infected cells were shown to be detectable at 4–5 days post-infection (p.i.) by monitoring syncytia formation, positive cells in immunofluorescence and p-24 production (assayed by the Abbott p-24 antigen test). The peak of HIV production was seen 10–15 days p.i. at which time virus was collected. After low speed centrifugation to remove debris, supernatants containing virus collected from infected cells were frozen in stocks at −90° C. One virus stock with endpoint titer of 40,000 50% tissue culture infective doses ($TCID_{50}$) was used throughout the studies (referred to as NT3-NT19).

EXAMPLE 9

HIV-1 Neutralization Assay

Sera containing antibodies that neutralize HTLV 111-B infectivity were detected by their ability to prevent HIV-1 syncytium formation, p-24 antigen production and decreased number of infected cells as determined by immunofluorescence markers, compared to control infections lacking peptide specific antisera. Stock virus, described in Example 8 was diluted to 100 $TCID_{50}$ and mixed with serial fourfold dilutione (1/5, 1/20, and 1/80) of complement-inactivated immunesera obtained from the monkeys immunized as described in Example 4. As a positive control, a guinea pig hyperimmune serum (referred to as MSV) with known HIV neutralizing titer of 1/40–1/160 was included in all experiments (kindly provided by Prof. B. Morein, Dept. Veterinary Virology, BMC, Uppsala, Sweden). After incubation for 60 min at 37° C. or 16 hours at 4° C., the serum-virus mixture was added to $1 \times 10^6$ H-9 cells and incubated for another 60 min at 37° C. Following incubation, the cells were washed once and placed in 24 well multidish plates with 2 ml of growth medium (RPMI, 10% FCS, 2 μg polybrene/ml) per well.

Cells were examined under the microscope (magnification ×200) for the presence of syncytia on days 5–12 p.i. Supernatants from infected cells were assayed for the presence of p-24 antigen according to the manufacturer's instructions (Abbott ag test HIVAG-1 ®, Enzyme Immunoassay for the Detection of Human Immunodeficiency Virus Type I (HIV-1) Antigen(s) in Human Serum or Plasma) in tenfold serial dilutions (1/10–1/1,000) at 10 days p.i. The results are presented as absorbance values at 454 nm with higher absorbance values indicating higher P-24 antigen concentration and hence HIV infection. Serial dilutions of the supernatants were made so as to detect p-24 concentrations in the most accurate range (<2.0 absorbance units).

The number of infected cells were determined at the end of experiment (usually on day 15 p.i.) by acetone-fixation of cells on slides adopted for immunofluorescence (IF). An indirect IF test was used according to standard procedures described in Jeansson et al., "Elimination of Mycoplasmas from Cell Cultures Utilizing Hyperimmune Sera", Ex. Cell Res., 161:181–188 (1985), with 1/400 dilution hyperimmune sera from HIV-infected individuals and a fluorescein isothiocyanate (FITC) labeled antihuman IgG antibody (Bio-Merieux France) diluted 1/100. Tables 5–8 show the results obtained from screening of hyperimmune sera from monkeys immunized with peptides 1–40.

In Tables 5(A–D)-8 the p24 antigen content of the supernatants was analyzed by ELISA, indirect IF and syncytia formation as described above. The relative amount of antigen positive cells is depicted as AG POS cells wherein the percentages are represented by: −=0%, +=>0-2%, ++=3-10% and +++=11-20% where the percentage interval indicates the number of antigen positive cells.

Table 5A (HIVNT3P1.XLS) depicts the results obtained with sera derived from monkeys immunized with peptides gp120-1–gp120-10. The cells used were H9 NY and the virus used was HTLV-IIIB, Batch 18 described in Example 8. The incubation protocol was (virus plus serum) incubation at 37° C. for one hour.

Table 5B (HIVNT4P1.XLS) depicts the results obtained with sera derived from monkeys immunized with peptides gp120-11–gp120-20. The cells used were H9 NY and the virus used was HTLV-IIIB, Batch 18 described in Example 8. The incubation protocol was (virus plus serum) incubation at 37° C. for one hour.

Table 5C (HIVNT5P1.XLS) depicts the results obtained with sera derived from monkeys immunized with peptides gp120-21–gp120-30. The cells used were H9 NY, and the virus used was HTLV-IIIB, Batch 18 described in Example 8. The incubation protocol used was virus plus serum incubated at 37° C. for one hour.

Table 5D (HIVNT6P1.XLS) depicts the results obtained with sera derived from monkeys immunized with peptides gp120-31–gp120-40.- The cells used were H9 NY and the virus used was HTLV-IIIB, Batch 18 described in Example 8. The incubation protocol was (virus plus serum) incubation at 37° C. for one hour.

Table 6 (HIVTAB4.XLS) shows the results of the first retest of putative neutralizing antibodies as determined by the first test (Tables 5A–D). In each test the virus used was HTLV-IIIB, Batch 18 and the cells used were H9 NY. The first retest results in rows 1–19 are the results of neutralization test number 5. The incubation protocol was incubation at 37° C. for one hour. The first retest results in rows 20–32 are the results of neutralization test number 7. The incubation protocol was incubation of at 37° C. for one hour.

Table 7 (HIVTAB5.XLS) shows second, third and fourth retest results of the positive peptides. In each test the virus used was HTLV-IIIB Batch 18 and the cells used were H9 NY. The second retest results in rows 1–4 are the results of neutralization test number 7. The incubation protocol was incubation at 37° C. for one hour. The second retest results in rows 5–13 are the results of neutralization test number 12. The third retest results are shown rows 14–16 are the results of neutralization test number 12. The incubation protocol was incubation at 37° C. for one hour. The fourth retest results in rows 17–39 are the results of neutralization test number 16. The incubation protocol was at 4° C. for 16 hours. The second retest results in rows 40–53 are the result of neutralization test 19. The incubation protocol was cells plus virus at 4° for 16 hours.

Table 8 (HIVKOMBP.XLS) shows the neutralization assay results with combined hyperimmune sera. Note that the incubation of virus and cells was at 4° C. for 16 hours.

The results depicted in Tables 5(A–D)-8 indicate that peptides gp120-12, gp120-16, and gp120-19 elicit the production of HIV neutralizing antibodies in primate subjects. The use of the peptides in vaccination of human subjects is therefore applicable to prevent infection by HIV or to induce heightened immune response in subjects already infected by HIV.

TABLE 5A

ASSAYS OF ANTISERA TO PEPTIDES gp120-1–gp120-10

| | PEPTIDE | Serum Dilution | P-24 ANTIGEN (Supernatant DIL) | | | RELATIVE AMOUNT OF AG POS CELLS |
|---|---|---|---|---|---|---|
| | | | 1/10 | 1/100 | 1/1000 | |
| 23. | | 1/20 | >2.0 | 0.448 | 0.082 | ++ |
| 24. | | 1/80 | >2.0 | 0.592 | 0.097 | ++ |
| 25. | preimmune | | >2.0 | 0.43 | 0.082 | ++ |
| 26. | gp120-5 | 1/5 | >2.0 | 0.638 | 0.098 | ++ |
| 27. | | 1/20 | >2.0 | 0.737 | 0.11 | ++ |
| 28. | | 1/80 | >2.0 | 0.786 | 0.119 | +++ |
| 29. | preimmune | | >2.0 | 0.822 | 0.125 | ++ |
| 30. | gp120-6 | 1/5 | >2.0 | 0.716 | 0.131 | +++ |
| 31. | | 1/20 | >2.0 | 0.977 | 0.119 | ++ |
| 32. | | 1/80 | >2.0 | 0.861 | 0.124 | ++ |
| 33. | preimmune | | >2.0 | 0.719 | 0.116 | ++ |
| 34. | gp120-7 | 1/5 | >2.0 | 0.587 | 0.106 | ++ |
| 35. | | 1/20 | >2.0 | 0.45 | 0.092 | ++ |
| 36. | | 1/80 | >2.0 | 0.756 | 0.117 | ++ |
| 37. | preimmune | | >2.0 | 0.507 | 0.096 | +++ |
| 38. | gp120-8 | 1/5 | >2.0 | 0.555 | 0.098 | ++ |
| 39. | | 1/20 | >2.0 | 0.59 | 0.103 | ++ |
| 40. | | 1/80 | >2.0 | 0.308 | 0.081 | ++ |
| 41. | preimmune | | >2.0 | 0.322 | 0.076 | +++ |
| 42. | gp120-9 | 1/5 | >2.0 | 0.358 | 0.09 | ++ |
| 43. | | 1/20 | >2.0 | 0.403 | 0.082 | +++ |
| 44. | | 1/80 | >2.0 | 0.612 | 0.102 | +++ |
| 45. | preimmune | | >2.0 | 0.747 | 0.127 | ++ |
| 46. | gp120-10 | 1/5 | >2.0 | 0.3 | 0.074 | ++ |
| 47. | | 1/20 | >2.0 | 0.426 | 0.092 | ++ |
| 48. | | 1/80 | >2.0 | 0.442 | 0.083 | ++ |

TABLE 5B

ASSAYS OF ANTISERA TO PEPTIDES gp120-11–gp120-20

| | PEPTIDE | Serum Dilution | P-24 ANTIGEN (Supernatant DIL) | | | RELATIVE AMOUNT OF AG POS CELLS |
|---|---|---|---|---|---|---|
| | | | 1/10 | 1/100 | 1/1000 | |
| 1. | pre-immune | 1/5 | >2.0 | 0.882 | 0.149 | ++ |
| 2. | gp120-11 | 1/5 | >2.0 | 0.73 | 0.135 | ++ |
| 3. | | 1/20 | >2.0 | 1.73 | 0.299 | ++ |
| 4. | | 1/80 | >2.0 | 0.700 | 0.148 | ++ |
| 5. | pre-immune | 1/5 | >2.0 | 1.07 | 0.151 | ++ |
| 6. | gp120-12 | 1/5 | 0.157 | 0.07 | 0.076 | + |
| 7. | | 1/20 | >2.0 | 1.45 | 0.22 | ++ |
| 8. | | 1/80 | >2.0 | 1.37 | 0.221 | ++ |
| 9. | pre-immune | 1/5 | >2.0 | 0.58 | 0.107 | ++ |
| 10. | gp120-13 | 1/5 | >2.0 | 1.16 | 0.194 | ++ |
| 11. | | 1/20 | 1.816 | 0.37 | 0.095 | ++ |
| 12. | | 1/80 | >2.0 | 1.16 | 0.187 | ++ |
| 13. | pre-immune | 1/5 | >2.0 | >2.0 | 0.281 | ++ |
| 14. | gp120-14 | 1/5 | >2.0 | 0.81 | 0.142 | ++ |
| 15. | | 1/20 | >2.0 | 1.39 | 0.219 | ++ |

TABLE 5B-continued
ASSAYS OF ANTISERA TO PEPTIDES gp120-11–gp120-20

| PEP-TIDE | Serum Dilution | P-24 ANTIGEN (Supernatant DIL) | | | RELATIVE AMOUNT OF AG POS CELLS |
|---|---|---|---|---|---|
| | | 1/10 | 1/100 | 1/1000 | |
| 16. | 1/80 | >2.0 | 0.83 | 0.156 | ++ |
| 17. pre-immune | 1/5 | >2.0 | 1.13 | 0.192 | ++ |
| 18. gp120-15 | 1/5 | >2.0 | 1.43 | 0.243 | +++ |
| 19. | 1/20 | 0.069 | 0.05 | 0.05 | − |
| 20. | 1/80 | >2.0 | 0.57 | 0.104 | ++ |
| 21. pre-immune | 1/5 | >2.0 | 1.78 | 0.303 | ++ |
| 22. gp120-16 | 1/5 | 0.26 | 0.07 | 0.056 | + |
| 23. | 1/20 | 0.067 | 0.06 | 0.054 | − |
| 24. | 1/80 | >2.0 | 0.74 | 0.132 | ++ |
| 25. pre-immune | 1/5 | >2.0 | 1.13 | 0.171 | ++ |
| 26. gp120-17 | 1/5 | >2.0 | 0.76 | 0.161 | ++ |
| 27. | 1/20 | >2.0 | 1.56 | 0.285 | ++ |
| 28. | 1/80 | >2.0 | 0.7 | 0.129 | ++ |
| 29. pre-immune | 1/5 | >2.0 | 1.41 | 0.177 | ++ |
| 30. gp120-18 | 1/5 | >2.0 | >2.0 | 0.339 | ++ |
| 31. | 1/20 | >2.0 | 1.36 | 0.218 | ++ |
| 32. | 1/80 | >2.0 | 1.26 | 0.199 | ++ |
| 33. pre-immune | 1/5 | >2.0 | 0.39 | 0.097 | ++ |
| 34. gp120-19 | 1/5 | 0.476 | 0.1 | 0.061 | + |
| 35. | 1/20 | 1.048 | 0.18 | 0.068 | + |
| 36. | 1/80 | >2.0 | 1.62 | 0.303 | ++ |
| 37. pre-immune | 1/5 | >2.0 | 1.11 | 0.189 | ++ |
| 38. gp120-20 | 1/5 | >2.0 | 1.19 | 0.182 | +++ |
| 39. | 1/20 | >2.0 | 1.47 | 0.054 | ++ |
| 40. | 1/80 | >2.0 | 1.42 | 0.264 | ++ |

TABLE 5C
ASSAY OF ANTISERA TO PEPTIDES 21-30

| | PEPTIDE | Serum Dilution | P-24 ANTIGEN (Supernatant DIL) | | | RELATIVE AMOUNT OF AG POS CELLS | NO. OF SYNCYTIA/WELL | |
|---|---|---|---|---|---|---|---|---|
| | | | 1/10 | 1/100 | 1/1000 | | Day 5 | Day 7 |
| 41. | pos control | | >2.0 | 0.65 | 0.09 | ++ | 12 | 72 |
| 42. | pos control | | 1.85 | 0.24 | 0.061 | ++ | 6 | 27 |
| 43. | neg control | | 0.4 | | | | 0 | 0 |
| 44. | guinea pig | 1/10 | 0.5 | 0.04 | 0.047 | − | 0 | 0 |
| 45. | pos control | 1/40 | 0.05 | 0.04 | 0.04 | − | 1 | 0 |
| 46. | antiserum | 1/160 | 0.04 | 0.05 | 0.043 | + | 1 | 3 |
| 47. | | 1/640 | 1.07 | 0.14 | 0.056 | + | 2 | 19 |
| 48. | preimmune | 1/5 | >2.0 | 1.57 | 0.275 | | 12 | 85 |
| 49. | gp120-21 | 1/5 | >2.0 | 0.4 | 0.075 | ++ | 3 | 28 |
| 50. | | 1/20 | 1 | 0.17 | 0.059 | | 5 | 21 |
| 51. | | 1/80 | >2.0 | 0.48 | 0.089 | | 7 | 72 |
| 52. | preimmune | 1/5 | >2.0 | 1.1 | 0.182 | | 3 | ND |
| 53. | gp120-22 | 1/5 | >2.0 | 1.48 | 0.221 | ++ | 2 | 75 |
| 54. | | 1/20 | >2.0 | 1.07 | 0.16 | | 0 | 80 |
| 55. | | 1/80 | >2.0 | 0.63 | 0.087 | | 5 | 90 |
| 56. | preimmune | 1/5 | >2.0 | 0.4 | 0.083 | | 4 | 52 |
| 57. | gp120-23 | 1/5 | 1.97 | 0.26 | 0.067 | ND | 0 | 20 |
| 58. | | 1/20 | >2.0 | 1.63 | 0.236 | | 5 | 98 |
| 59. | | 1/80 | >2.0 | 0.35 | 0.084 | | 5 | >150 |
| 60. | preimmune | 1/5 | >2.0 | >2.0 | 0.355 | | 2 | 49 |
| 61. | gp120-24 | 1/5 | 1.95 | 0.29 | 0.067 | + | 0 | 3 |
| 62. | | 1/20 | >2.0 | 0.37 | 0.081 | | 5 | 34 |
| 63. | | 1/80 | 1.87 | 0.24 | 0.069 | | 3 | 48 |
| 64. | preimmune | 1/5 | >2.0 | 0.83 | 0.145 | | 0 | 91 |
| 65. | gp120-25 | 1/5 | >2.0 | 0.73 | 0.11 | ++ | 1 | 25 |
| 66. | | 1/20 | 1.63 | 0.23 | 0.062 | | 0 | 15 |
| 67. | | 1/80 | 1.88 | 0.22 | 0.064 | | 0 | 38 |
| 68. | preimmune | 1/5 | >2.0 | 0.48 | 0.089 | | 0 | 79 |
| 69. | gp120-26 | 1/5 | >2.0 | 0.62 | 0.101 | ++ | 3 | 91 |
| 70. | | 1/20 | >2.0 | 0.34 | 0.063 | | 3 | 35 |
| 71. | gp120-26 | 1/80 | 1.27 | 0.19 | 0.061 | | 0 | 21 |
| 72. | preimmune | 1/5 | >2.0 | 0.66 | 0.11 | | 2 | 52 |
| 73. | gp120-27 | 1/5 | >2.0 | 0.58 | 0.098 | ++ | 1 | 26 |
| 74. | | 1/20 | >2.0 | 0.65 | 0.099 | | 6 | 49 |
| 75. | | 1/80 | >2.0 | 0.3 | 0.062 | | 2 | 35 |
| 76. | preimmune | 1/5 | >2.0 | >2.0 | 0.317 | | 7 | 31 |
| 77. | gp120-28 | 1/5 | >2.0 | 0.39 | 0.078 | ++ | 2 | 22 |
| 78. | | 1/20 | >2.0 | 0.68 | 0.105 | | 5 | 70 |
| 79. | | 1/80 | 0.99 | 0.15 | 0.05 | | 3 | >150 |
| 80. | preimmune | 1/5 | >2.0 | 1.29 | 0.187 | | 5 | 97 |
| 81. | gp120-29 | 1/5 | >2.0 | 0.55 | 0.096 | ++ | 3 | 112 |
| 82. | | 1/20 | >2.0 | 0.85 | 0.135 | | 3 | >150 |
| 83. | | 1/80 | >2.0 | 0.72 | 0.113 | | 0 | 29 |
| 84. | preimmune | 1/5 | >2.0 | >2.0 | 0.326 | | 10 | 130 |
| 85. | gp120-30 | 1/5 | >2.0 | 0.27 | 0.073 | + | 3 | 38 |
| 86. | | 1/20 | >2.0 | 1.71 | 0.24 | | 9 | 52 |
| 87. | | 1/80 | >2.0 | 0.44 | 0.082 | | 6 | ND |

TABLE 5D

ASSAYS OF ANTISERA TO PEPTIDES 31-40

| | PEPTIDE | Serum Dilution | P-24 ANTIGEN (Supernatant DIL) | | | RELATIVE AMOUNT OF AG POS CELLS | NO. OF SYNCYTIA/WELL Day 6 |
|---|---|---|---|---|---|---|---|
| | | | 1/10 | 1/100 | 1/1000 | | |
| 88. | pos control | | 0.976 | 0.258 | 0.123 | | 6 |
| 89. | pos control | | 1.836 | 0.656 | 0.185 | | 11 |
| 90. | neg control | | | | | | |
| 91. | guinea pig | 1/10 | 0.103 | 0.088 | 0.09 | | 0 |
| 92. | pos control | 1/40 | 0.104 | 0.087 | 0.093 | | 0 |
| 93. | antiserum | 1/160 | 0.749 | 0.29 | 0.1 | | 4 |
| 94. | | 1/640 | 1.066 | 0.238 | 0.237 | | 7 |
| 95. | preimmune | 1/5 | 0.824 | | | | |
| 96. | gp120-31 | 1/5 | 1.769 | 0.675 | 0.186 | | 47 |
| 97. | | 1/20 | 1.124 | 0.302 | 0.111 | | 22 |
| 98. | | 1/80 | 0.978 | 0.258 | ND | | 24 |
| 99. | preimmune | 1/5 | 0.883 | | | | |
| 100. | gp120-32 | 1/5 | 1.163 | 0.258 | ND | | 7 |
| 101. | | 1/20 | 1.482 | 0.311 | ND | | 8 |
| 102. | | 1/80 | 0.996 | 0.263 | ND | | 0 |
| 103. | preimmune | 1/5 | 1.76 | | | | |
| 104. | gp120-33 | 1/5 | 0.84 | 0.239 | 0.156 | | 20 |
| 105. | | 1/20 | 1.282 | 0.333 | 0.144 | | 16 |
| 106. | | 1/80 | 0.76 | 0.207 | ND | | 17 |
| 107. | preimmune | 1/5 | ND | | | | |
| 108. | gp120-34 | 1/5 | 0.293 | 0.134 | 0.12 | | 18 |
| 109. | | 1/20 | 1.446 | 0.391 | 0.148 | | 17 |
| 110. | | 1/80 | 0.42 | 0.15 | ND | | |
| 111. | preimmune | 1/5 | ND | | | | |
| 112. | gp120-35 | 1/5 | 1.485 | 0.52 | 0.142 | | 10 |
| 113. | | 1/20 | 1.778 | 0.873 | 0.194 | | 26 |
| 114. | | 1/80 | 1.475 | 0.196 | ND | | |
| 115. | preimmune | 1/5 | 1.076 | | | | |
| 116. | gp120-36 | 1/5 | 0.957 | 0.26 | 0.149 | | 28 |
| 117. | | 1/20 | 1.44 | 0.448 | 0.119 | | 16 |
| 118. | | 1/80 | 1.148 | 0.486 | ND | | |
| 119. | preimmune | 1/5 | 1.563 | | | | |
| 120. | gp120-37 | 1/5 | 0.666 | 0.155 | 0.098 | | 15 |
| 121. | | 1/20 | 1.143 | 0.33 | 0.129 | | 12 |
| 122. | | 1/80 | 1.362 | 0.33 | ND | | |
| 123. | preimmune | 1/5 | 1.364 | | | | |
| 124. | gp120-38 | 1/5 | 1.386 | 0.59 | 0.114 | | 11 |
| 125. | | 1/20 | 0.576 | 0.214 | 0.106 | | 17 |
| 126. | | 1/80 | 1.23 | 0.329 | ND | | |
| 127. | preimmune | 1/5 | 1.854 | | | | |
| 128. | gp120-39 | 1/5 | 1.376 | 0.495 | 0.182 | | 28 |
| 129. | | 1/20 | 0.711 | 0.296 | 0.118 | | 17 |
| 130. | | 1/80 | 0.929 | 0.237 | ND | | |
| 131. | preimmune | 1/5 | ND | | | | |
| 132. | gp120-40 | 1/5 | 0.862 | 0.255 | 0.132 | | 13 |
| 133. | | 1/20 | 0.989 | 0.273 | 0.143 | | 10 |
| 134. | | 1/80 | 0.477 | 0.164 | ND | | |

TABLE 6

RETESTING OF HYPERIMMUNE SERA WITH THE CAPACITY TO NEUTRALIZE HIV

| | PEPTIDE | Serum Dilution | P-24 ANTIGEN (DIL) | | | RELATIVE AMOUNT OF AG POS CELLS | NO. OF SYNCYTIA/WELL | |
|---|---|---|---|---|---|---|---|---|
| | | | 1/10 | 1/100 | 1/1000 | | Day 5 | Day 7 |
| First Retest | | | | | | | | |
| 1. | pos control | | >2.0 | 0.646 | 0.09 | ++ | 12 | 72 |
| 2. | pos control | | 1.853 | 0.244 | 0.061 | ++ | 6 | 27 |
| 3. | neg control | | 0.039 | | | | 0 | 0 |
| 4. | guinea pig | 1/10 | 0.051 | 0.04 | 0.047 | — | 0 | 0 |
| 5. | pos control | 1/40 | 0.052 | 0.042 | 0.04 | — | 1 | 0 |
| 6. | antiserum | 1/160 | 0.042 | 0.046 | 0.043 | + | 1 | 3 |
| 7. | | 1/640 | 1.067 | 0.144 | 0.056 | + | 2 | 19 |
| 8. | preimmune | 1/5 | 2 | 1.326 | 0.172 | | 10 | 112 |
| 9. | gp120-12 | 1/5 | 1.083 | 0.153 | 0.06 | + | 1 | 24 |
| 10. | | 1/20 | 2 | 1.487 | 0.171 | | 7 | 175 |
| 11. | | 1/80 | 2 | 0.463 | 0.07 | | 6 | ND |
| 12. | preimmune | 1/5 | 2 | 1.991 | 0.237 | | 2 | 64 |
| 13. | gp120-16 | 1/5 | 2 | 0.355 | 0.07 | + | 0 | 13 |
| 14. | | 1/20 | 0.741 | 0.103 | 0.048 | | 0 | 11 |
| 15. | | 1/80 | 2 | 0.32 | 0.08 | | 0 | 35 |
| 16. | preimmune | 1/5 | >2.0 | 0.547 | 0.082 | | 3 | 42 |
| 17. | gp120-19 | 1/5 | 0.141 | 0.062 | 0.053 | + | 0 | 6 |
| 18. | | 1/20 | 1.134 | 0.164 | 0.054 | | 0 | 26 |
| 19. | | 1/80 | >2.0 | 0.455 | 0.081 | | 1 | 45 |

TABLE 6-continued

RETESTING OF HYPERIMMUNE SERA WITH THE CAPACITY TO NEUTRALIZE HIV

| First Retest | | 1/5 | 1/50 | 1/500 | | Day 7 | Day 10 |
|---|---|---|---|---|---|---|---|
| 20. pos control | | 1.175 | 0.426 | 0.201 | | 9 | 46 |
| 21. pos control | | 1.529 | 0.401 | 0.161 | | 32 | 167 |
| 22. neg control | | | | | | | |
| 23. guinea pig | 1/10 | 0.139 | 0.165 | 0.145 | — | 0 | 0 |
| 24. pos control | 1/40 | 0.211 | 0.159 | 0.168 | — | 1 | 0 |
| 25. antiserum | 1/160 | 0.961 | 0.299 | 0.163 | ++ | 9 | 26 |
| 26. | 1/640 | 0.989 | 0.26 | 0.159 | ++ | 5 | 20 |
| 27. gp120-24 | 1/5 | 1.067 | 0.245 | 0.166 | ++ | 4 | 34 |
| 28. | 1/20 | 0.795 | 0.204 | 0.167 | ++ | 5 | 41 |
| 29. | 1/80 | 0.433 | 0.167 | | — | 15 | 80 |
| 30. gp120-25 | 1/5 | 1.237 | 0.282 | 0.155 | ++ | 19 | 144 |
| 31. | 1/20 | 1.312 | 0.373 | 0.187 | ++ | 42 | 116 |
| 32. | 1/80 | ND | ND | ND | — | ND | ND |

TABLE 7

RETESTING OF HYPERIMMUNE SERA WITH CAPACITY TO NEUTRALIZE HTLV-III

| | | P-24 ANTIGEN (Supernatant DIL) | | | *RELATIVE AMOUNT | NO. OF SYNCYTIA/WELL | |
|---|---|---|---|---|---|---|---|
| PEPTIDE | SERUM DILUTION | 1/5 | 1/50 | 1/500 | OF AG POS CELLS | Day 5 | Day 7 |
| Second Retest | | | | | | | |
| 1. gp120-16 | 1/5 | ND | ND | ND | | ND | ND |
| 2. | 1/5 | 1.924 | 1.062 | 0.282 | ++ | | |
| 3. | 1/20 | 0.365 | 0.172 | 0.145 | — | 2 | 5 |
| 4. | 1/80 | 0.163 | 0.133 | | — | 0 | 0 |
| Second Retest | | 1/10 | 1/100 | 1/1,000 | | | |
| 5. pos control | | >2.0 | >2.0 | 1.026 | +++ | 320 | |
| 6. pos control | | >2.0 | >2.0 | 0.639 | +++ | 220 | |
| 7. pos control | | >2.0 | >2.0 | 0.866 | +++ | 290 | |
| 8. pos control | | >2.0 | >2.0 | 0.881 | +++ | | |
| 9. neg control | | 0.223 | | | — | | |
| 10. neg control | | 0.16 | | | — | | |
| 11. gp120-24 | 1/5 | >2.0 | >2.0 | 0.545 | +++ | 112 | |
| 12. | 1/20 | >2.0 | >2.0 | 0.819 | +++ | 138 | |
| 13. | 1/80 | >2.0 | >2.0 | | +++ | 230 | |
| Third Retest | | | | | | | |
| 14. gp120-16 | 1/5 | 0.122 | 0.1 | 0.115 | — | 0 | |
| 15. | 1/20 | >2.0 | 1.14 | 0.352 | ++ | 0 | |
| 16. | 1/80 | >2.0 | >2.0 | | +++ | 210 | |
| Fourth Retest | | | | | | | |
| 17. pos control | | 1.425 | 0.732 | 0.154 | ++ | 16 | |
| 18. pos control | | 1.346 | 0.672 | 0.152 | +++ | 16 | |
| 19. pos control | | 1.431 | 0.845 | 0.182 | +++ | 17 | |
| 20. pos control | | 1.414 | 0.931 | 0.251 | | | |
| 21. neg control | | 0.067 | | | — | | |
| 22. neg control | | 0.045 | | | — | | |
| 23. neg control | | 0.042 | | | — | | |
| 24. guinea pig | 1/10 | 0.044 | 0.037 | 0.029 | | 0 | |
| 25. pos control | 1/40 | 0.063 | 0.039 | 0.029 | | 0 | |
| 26. antiserum | 1/160 | 0.036 | 0.035 | 0.055 | | 0 | |
| 27. | 1/640 | 0.556 | 0.072 | 0.034 | 1 | | |
| 28. gp120-12 | 1/8 | 0.072 | 0.043 | 0.046 | | 0 | |
| 29. | 1/32 | 0.169 | 0.054 | 0.047 | | 0 | |
| 30. | 1/128 | >2.0 | 1.124 | 0.241 | | 19 | |
| 31. gp120-16 | 1/8 | 0.043 | 0.045 | 0.049 | | 0 | |
| 32. | 1/32 | 0.052 | 0.043 | 0.048 | | 0 | |
| 33. | 1/128 | 1.54 | 0.903 | 0.014 | | 4 | |
| 34. gp120-19 | 1/8 | 0.105 | 0.043 | 0.042 | | 0 | |
| 35. | 1/32 | 0.358 | 0.08 | 0.045 | | 5 | |
| 36. | 1/128 | >2.0 | 0.944 | 0.205 | | 25 | |
| 37. gp120-24 | 1/8 | >2.0 | 0.885 | 0.155 | | 2 | |
| 38. | 1/32 | >2.0 | 1.174 | 0.293 | | 15 | |
| 39. | 1/128 | 1.158 | 0.858 | 0.213 | | 11 | |
| Second Retest | | 1/5 | 1/50 | 1/500 | | Day 5 | Day 7 |
| 40. pos control | | 0.916 | 0.166 | 0.099 | | | 74 |
| 41. pos control | | 1.607 | 0.469 | 0.151 | | | 130 |
| 42. pos control | | >2.0 | 0.943 | 0.203 | | | 123 |
| 43. pos control | | 1.445 | 0.319 | 0.082 | | | 195 |
| 44. neg control | | 0.145 | | | | | |
| 45. neg control | | 0.328 | | | | | |
| 46. guinea pig | 1/10 | 0.09 | 0.111 | 0.075 | | | 0 |
| 47. pos control | 1/140 | 0.096 | 0.082 | 0.078 | | | 0 |
| 48. antiserum | 1/160 | 0.094 | 0.109 | 0.091 | | | 0 |

TABLE 7-continued

| | | RETESTING OF HYPERIMMUNE SERA WITH CAPACITY TO NEUTRALIZE HTLV-III | | | | |
|---|---|---|---|---|---|---|
| 49. | | 1/640 | 0.996 | 0.212 | 0.104 | 35 |
| 50. | preimmune | 1/5 | >2.0 | 0.444 | 0.162 | 95 |
| 51. | gp120-15 | 1/5 | 0.155 | 0.094 | 0.111 | ND |
| 52. | | 1/20 | 0.152 | 0.109 | 0.158 | 4 |
| 53. | | 1/80 | 0.176 | 0.13 | 0.207 | 0 |

TABLE 8

| | | COMBINED NEUTRALIZED EFFECTS OF SERA FROM MONKEYS | | | | | |
|---|---|---|---|---|---|---|---|
| | PEPTIDE | Serum Dilution | P-24 ANTIGEN (Supernatant DIL) | | | NT TITRE OF SERUM | RELATIVE AMOUNT OF AG POS CELLS | NO. OF SYNCYTIA/WELL Day 6 |
| | | | 1/5 | 1/50 | 1/500 | | | |
| 1. | Pos control | | 1.4 | 0.7 | 0.154 | | ++ | 16 |
| 2. | Pos control | | 1.3 | 0.7 | 0.152 | | +++ | 16 |
| 3. | Pos control | | 1.4 | 0.8 | 0.182 | | | 17 |
| 4. | Pos control | | 1.4 | 0.9 | 0.251 | | | |
| 5. | neg control | | 0.1 | | | | − | |
| 6. | neg control | | 0 | | | | − | |
| 7. | neg control | | 0 | | | | − | |
| 8. | guinea pig | 1/10 | 0 | 0 | 0.029 | | | 0 |
| 9. | pos control | 1/40 | 0.1 | 0 | 0.029 | | | 0 |
| 10. | antiserum | 1/160 | 0 | 0 | 0.055 | 160 | | 0 |
| 11. | | 1/640 | 0.6 | 0.1 | 0.034 | | | 1 |
| 12. | Group I | 1/8 | 0 | 0 | 0.038 | | | 1 |
| 13. | gp120.mix | 1/32 | 0 | 0 | 0.041 | | | 0 |
| 14. | 12 + 16 + 19 + 24 | 1/128 | 0.2 | 0.1 | 0.043 | >128 | − | 0 |
| 15. | Group II | 1/8 | 0.1 | 0 | 0.046 | | | 0 |
| 16. | gp120.mix | 1/32 | 0.1 | 0.1 | 0.046 | | − | 0 |
| 17. | 16 + 19 | 1/128 | 0.1 | 0.2 | 0.043 | >128 | − | 0 |

We claim:

1. A peptide having the amino acid sequence X-Ser-Ser-Ser-Gly-Arg-Met-Ile-Met-Glu-Lys-Gly-Glu-Ile-Lys-Asn-Cys-Ser -Phe-Asn-Ile-Ser-Thr-Ser-Y wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group.

2. A peptide having the amino acid sequence X-Gly-Glu-Ile-Lys-Asn-Cys-Ser-Phe-Asn-Ile-Ser-Thr-Ser-Ile-Arg-Gly-Lys -Val-Gln-Lys-Glu-Tyr-Ala-Phe-Phe-Y wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group.

3. A peptide having the amino acid sequence X-Ile-Arg-Gly-Lys-Val-Gln-Lys-Glu-Tyr-Ala-Phe-Phe-Tyr-Lys-Leu-Asp-Ile -Ile-Pro-Ile-Asp-Asn-Asp-Thr-Thr-Ser-Tyr-Thr-Y wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group.

4. A peptide having the amino acid sequence X-Pro-Lys-Val-Ser-Phe-Glu-Pro-Ile-Pro-Ile-His-Tyr-Cys-Ala-Pro-Ala-Gly -Phe-Ala-Ile-Leu-Lys-Cys-Asn-Asn-Y wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group.

5. A peptide having the amino acid sequence X-Cys-Gly-Gly-Glu-Phe-Phe-Tyr-Cys-Asn-Ser-Thr-Gln-Leu-Phe-Asn-Ser-Thr -Trp-Phe-Asn-Ser-Thr-Trp-Y wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group.

6. A composition for the activation of T cells against human immunodeficiency virus comprising:
   (a) an amount of a peptide sufficient to elicit T cell activation, the peptide having the amino acid sequence:

X-Ser-Ser-Ser-Gly-Arg-Met-Ile-Met-Glu-Lys-Gly-
      Glu-Ile-Lys-Asn-Cys
      -Ser-Phe-Asn-Ile-Ser-Thr-Ser-Y, wherein X is either a hydrogen atom of the amino terminal NH₂ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group; and
   (b) a physiologically acceptable carrier therefor.

7. A composition for the activation of T cells against human immunodeficiency virus comprising:
   (a) an amount of a peptide sufficient to elicit T cell activation, the peptide having the amino acid sequence:

X-Gly-Glu-Ile-Lys-Asn-Cys-Ser-Phe-Asn-Ile-Ser-
Thr-Ser-Ile-Arg-Gly
-Lys-Val-Gln-Lys-Glu-Tyr-Ala-Phe-Phe-Y, wherein X is either a hydrogen atom of the amino terminal NH$_2$ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group; and (b) a physiologically acceptable carrier therefor.

8. A composition for the activation of T cells against human immunodeficiency virus comprising:

(a) an amount of a peptide sufficient to elicit T cell activation, the peptide having the amino acid sequence:

X-Ile-Arg-Gly-Lys-Val-Gln-Lys-Glu-Tyr-Ala-Phe-
Phe-Tyr-Lys-Leu-Asp
-Ile-Ile-Pro-Ile-Asp-Asn-Asp-Thr-Thr-Ser-Tyr-
Thr-Y, wherein X is either a hydrogen atom of the amino terminal NH$_2$ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group; and (b) a physiologically acceptable carrier therefor.

9. A composition for the induction of IL-2 production comprising:

(a) an amount of a peptide sufficient to elicit IL-2 production, the peptide having the amino acid sequence:

X-Pro-Lys-Val-Ser-Phe-Glu-Pro-Ile-Pro-Ile-His-
Tyr-Cys-Ala-Pro-Ala
-Gly-Phe-Ala-Ile-Leu-Lys-Cys-Asn-Asn-Y, wherein X is either a hydrogen atom of the amino terminal NH$_2$ group of said peptide or an additional amino acid selected to facilitate coupling of said peptide to a carrier and Y is selected from the group consisting of an amino group, a hydroxy group, a Cysteine residue, a Cysteine residue followed by a hydroxy group; and (b) a physiologically acceptable carrier therefor.

10. A composition for the activation of T cells against human immunodeficiency virus comprising:

(a) an amount of a peptide sufficient to elicit T cell activation, the peptide having the amino acid sequence:

X-Cys-Gly-Gly-Glu-Phe-Phe-Tyr-Cys-Asn-Ser-
Thr-Gln-Leu-Phe-Asn-Ser
-Thr-Trp-Phe-Asn-Ser-Thr-Trp-Y, wherein X is either a hydrogen atom of the amino terminal NH$_2$ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group; and (b) a physiologically acceptable carrier therefor.

11. A composition for the activation of T cells against human immunodeficiency virus comprising:

(a) an amount of at least two peptides sufficient to elicit T cell activation, wherein the peptides are selected from the amino acid sequences:

X—Ser—Ser—Ser—Gly—Arg—Met—Ile—Met—Glu—Lys—Gly—Glu—Ile—Lys—Asn—
Cys—Ser—Phe—Asn—Ile—Ser—Thr—Ser—Y;
X—Gly—Glu—Ile—Lys—Asn—Cys—Ser—Phe—Asn—Ile—Ser—Thr—Ser—Ile—Arg—
Gly—Lys—Val—Gln—Lys—Glu—Tyr—Ala—Phe—Phe—Y;
X—Ile—Arg—Gly—Lys—Val—Gln—Lys—Glu—Tyr—Ala—Phe—Phe—Tyr—Lys—Leu—
Asp—Ile—Ile—Pro—Ile—Asp—Asn—Asp—Thr—Thr—Ser—Tyr—Thr—Y;
and
X—Cys—Gly—Gly—Glu—Phe—Phe—Tyr—Cys—Asn—Ser—Thr—Gln—Leu—Phe—Asn—
Ser—Thr—Trp—Phe—Asn—Ser—Thr—Trp—Y wherein X is either a hydrogen atom of the amino terminal NH$_2$ group of said peptide or an additional amino acid selected to facilitate coupling of said peptide to a carrier and Y is selected from the group consisting of an amino group, a hydroxy group, a Cysteine residue, a Cysteine residue followed by an amino group and a Cysteine residue followed by a hydroxy group; and (b) a physiologically acceptable carrier therefor.

* * * * *